United States Patent
West et al.

(10) Patent No.: US 8,685,386 B2
(45) Date of Patent: Apr. 1, 2014

(54) METHODS AND COMPOSITIONS FOR IN VITRO AND IN VIVO CHONDROGENESIS

(75) Inventors: Michael D. West, Mill Valley, CA (US); Hal Sternberg, Berkeley, CA (US); Karen B. Chapman, Mill Valley, CA (US)

(73) Assignee: BioTime, Inc, Alameda, CA (US)

( * ) Notice: Subject to any disclaimer, the term of this patent is extended or adjusted under 35 U.S.C. 154(b) by 0 days.

(21) Appl. No.: 13/384,289

(22) PCT Filed: Jul. 16, 2010

(86) PCT No.: PCT/US2010/042369
§ 371 (c)(1),
(2), (4) Date: Mar. 16, 2012

(87) PCT Pub. No.: WO2011/009106
PCT Pub. Date: Jan. 20, 2011

(65) Prior Publication Data
US 2012/0171171 A1 Jul. 5, 2012

Related U.S. Application Data

(60) Provisional application No. 61/226,237, filed on Jul. 16, 2009, provisional application No. 61/243,939, filed on Sep. 18, 2009, provisional application No. 61/349,088, filed on May 27, 2010, provisional application No. 61/365,308, filed on Jul. 16, 2010.

(51) Int. Cl.
*C12N 5/073* (2010.01)
*A61K 35/12* (2006.01)

(52) U.S. Cl.
USPC ............... 424/93.1; 424/93.21; 424/93.7

(58) Field of Classification Search
CPC .............. A61K 35/28; A61K 38/1709; A61K 39/39541; C07K 2317/21; C12N 5/0696; C12N 5/0602; C12N 5/0606; C12N 5/0663
USPC ........ 435/325, 366, 377, 7.21; 424/93.7, 400, 424/465, 9.1, 93.1, 93.21

See application file for complete search history.

(56) References Cited

U.S. PATENT DOCUMENTS

2006/0073588 A1 * 4/2006 Adkisson et al. ............. 435/366

FOREIGN PATENT DOCUMENTS

WO    WO 2006138552 A2 * 12/2006 .............. A61L 27/38

OTHER PUBLICATIONS

Li et al, Biomaterials, 2005, 26:5158-5166.*
West et al, Regen Med, 2008, 3:287-308.*
Johnstone et al, Experimental Cell Research, 1998, 238:265-272.*
Winter et al, Arthritis and Rheumatism, 2003, 48:418-429.*
Levenberg et al, PNAS, 2003, 100:12741-12746.*
Pelttari et al, Arthritis and Rheumatism, 2006, 54:3254-3266.*
Ofek et al, Journal of Biomechanical Engineering, 2009, 131:061011-1-061011-8.*
Sternberg et al, Regen Med, 2013, 8:125-144.*
Sternberg et al, Regen Med, 2012, 7:481-501.*
Assady et al. "Insulin Production by Human Embryonic Stem Cells," Diabetes (2001) 50:1691.
Boheler et al. "Differentiation of Pluripotent Embryonic Stem Cells into Cardiomyocytes," Circ. Res. 91:189, (2002).
Itskovitz-Elder et al. "Differentiation of Human Embryonic Stem Cells into Embryoid Bodies Comprising the Three Embryonic Germ Layers," Mol. Med. 6:88, (2000).

* cited by examiner

*Primary Examiner* — Valarie Bertoglio
*Assistant Examiner* — Chi-Feng Hsu
(74) *Attorney, Agent, or Firm* — E. Stewart Mittler

(57) ABSTRACT

Aspects of the present invention include methods and compositions related to the production, identification and use of embryonic progenitor cell lines that are capable of undergoing chondrogenesis. A number of exemplary chondrogenic cell lines derived from primordial stem cells are disclosed. The chondrogenic cell lines described herein are robust, can expand for >40 passages, and have site-specific purity, thus providing for compositions and methods of producing diverse cartilage types with unique molecular compositions for use in research and therapy.

6 Claims, 6 Drawing Sheets

METHODS AND COMPOSITIONS FOR IN VITRO AND IN VIVO CHONDROGENESIS

CROSS REFERENCE

This application claims the benefit under 35 U.S.C. §119(e) of the following provisional patent applications: Application Ser. No. 61/226,237, entitled "Methods and Compositions Useful for In Vitro and In Vivo Chondrogenesis Using Embryonic Progenitor Cell Lines" filed Jul. 16, 2009; Application Ser. No. 61/243,939, entitled "Improved Methods of Screening Embryonic Progenitor Cell Lines" filed Sep. 18, 2009; Application Ser. No. 61/349,088, entitled "Improved Methods of Screening Embryonic Progenitor Cell Lines" filed May 27, 2010; and Application Ser. No. 61/365,308, entitled "Methods and Compositions for In Vitro and In Vivo Chondrogenesis" filed Jul. 16, 2010. The entirety of each of these applications is incorporated herein by reference.

BACKGROUND

The limited regenerative capacity of cartilage limits the body's natural capacity to repair damage due to trauma or degenerative disease. For example, osteoarthritis (OA) afflicts up to 70% of individuals over 65 years of age (21 million Americans). Injury to the meniscus or anterior cruciate ligament often leaves the patient at increased risk of arthritis. Osteoarthritis is characterized by a progressive loss of cartilage on the articular surface, leading to a painful exposure of subchondral bone. Following this injury to the articular cartilage, human tissues shows little repair capacity. The nascent cartilage that does appear as a result on an innate repair response is generally fibrous in nature and hence unsuitable for repair.

Various therapeutic regimens have been developed for treating subjects having cartilage damage. Examples of these treatments include those that are intended to trigger cartilage production in the subject using mechanical means (e.g., abrasion and microfracture surgery, such as drilling, microfracture surgery, chondroplasty, and spongialization; laser-assisted treatments, which combine the removal of diseased cartilage with cartilage reshaping) and therapies that rely on transplantation (or grafting) of tissue to the damaged site (e.g., periosteal grafting, osteochondral grafting (mosaicplasty), and articular cartilage paste grafting). Success rates of these therapies vary and some have potential deleterious side effects, including tissue necrosis, reactive synovitis, chondrolysis, and an acceleration of articular cartilage degeneration.

A cell-based cartilage treatment regimen, known as autologous chondrocyte therapy (ACT), involves the removal of chondrocytes from cartilage, the expansion of the cells in vitro, and the administration of these expanded cells into the patient with or without a supporting matrix (or other proteins or proteoglycans). ACT therapy is complicated by the dedifferentiation of human articular chondrocytes when cultured in vitro as well as the relative difficulty of re-differentiating the cells such that they produce abundant cartilage matrix at the graft site. Further, only a small amount of cartilage can be collected from humans, and thus only a small number of chondrocytes can be used for the initiation of the culture. Thus, there is continued difficulty in applying isolated human chondrocytes to transplantation therapy in practice.

Another therapeutic strategy is the utilization of bone marrow-derived mesenchymal stem cells (hbmMSCs). Clinical studies utilizing a single dose of hbmMSCs, (Chondrogen) show a reduction in pain compared to hyaluronic acid (HA) control. However, Mesenchymal stem cells (MSCs) have two hurdles in regard to their use in regenerating cartilage. First, the use of the cells as an allogeneic graft is problematic due to the limited proliferative capacity of adult MSCs, and even if the cells are capable of a certain amount of expansion, they often relatively quickly lose their capacity to form cartilage. The second hurdle is that MSCs, such as bone marrow-derived MSCs form hypertrophic chondrocytes, characterized by high levels of COL10A1 and IHH expression. The role of these chondrocytes in development are to recruit blood vessels and osteoblasts and then die. Hypertrophic chondrocytes are observed for instance in the growth plate regions of long bones. They are also observed at the site of a bone fracture where they similarly play an important role in bone formation. Therefore, the use of MSCs in the treatment of trauma or degenerative diseases of cartilage, such as osteoarthritis have yielded mixed results. In addition, there are numerous types of cartilage in the body. The elastic cartilage of the ear has differing molecular composition than that of the nose, sternum, trachea, and weight-bearing joints.

Therefore, the field of regenerative medicine, particularly in the field of cartilage regeneration and repair, are in great need of novel cellular formulations to generate commercial quantities of diverse types of permanent, as opposed to hypertrophic, chondrocytes.

SUMMARY

Aspects of the present invention include methods and compositions related to the production, identification and use of embryonic progenitor cell lines that are capable of undergoing chondrogenesis. A number of exemplary chondrogenic cell lines derived from primordial stem cells are disclosed. The chondrogenic cell lines described herein are robust, can expand for >40 passages, and have site-specific purity, thus providing for compositions and methods of producing diverse cartilage types with unique molecular compositions for use in research and therapy.

ABBREVIATIONS

Figure 1:
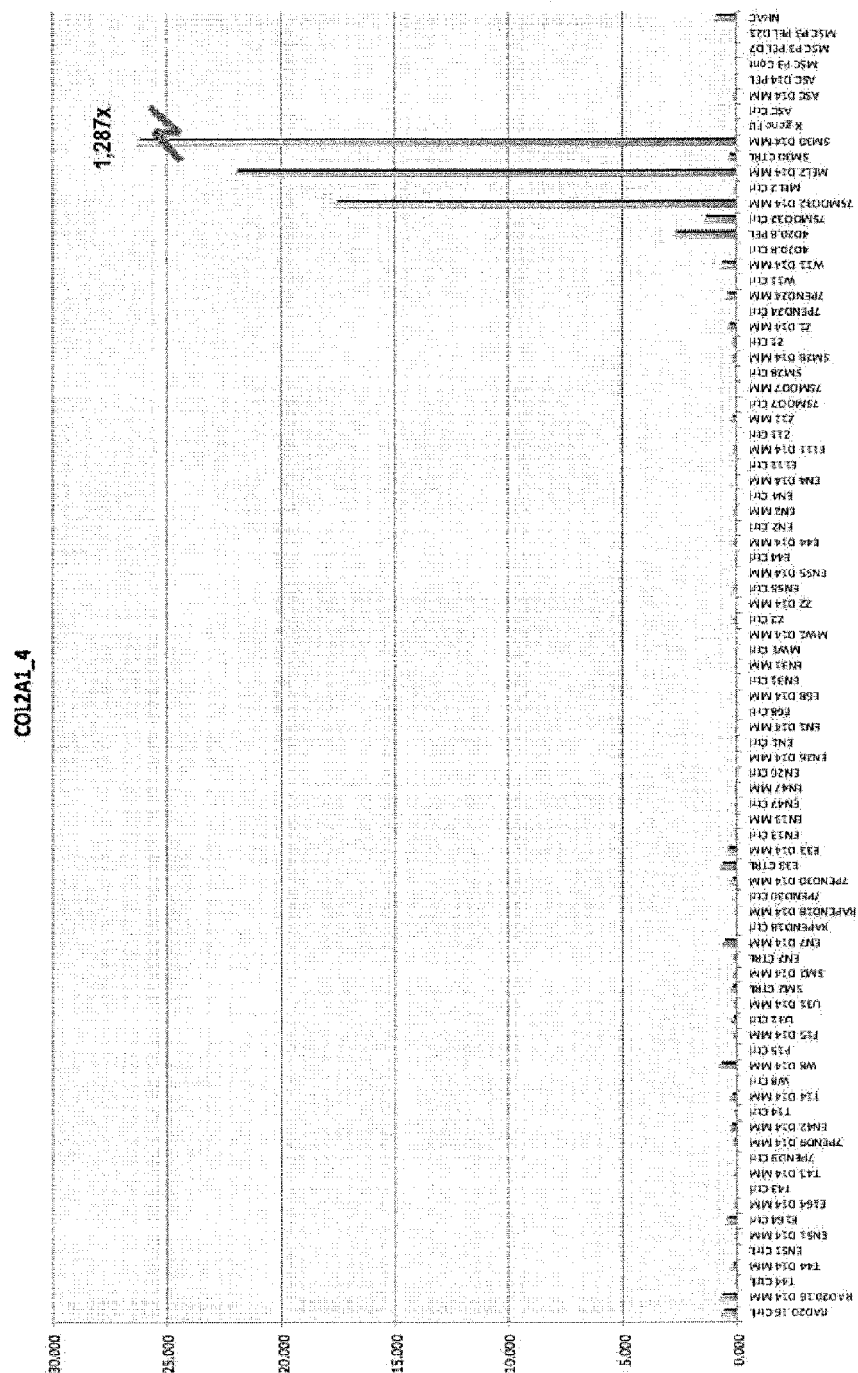
FIG. 1: Levels of induction of COL2A1 in lines assayed by qPCR before and after 14 days of chondrogenic micromass conditions.

AFP—Alpha fetoprotein
BMP—Bone Morphogenic Protein
BRL—Buffalo rat liver
BSA—Bovine serum albumin CD—Cluster Designation
cGMP—Current Good Manufacturing Processes
CNS—Central Nervous System
DMEM—Dulbecco's modified Eagle's medium
DMSO—Dimethyl sulphoxide
DPBS—Dulbecco's Phosphate Buffered Saline
EC—Embryonal carcinoma
EC Cells—Embryonal carcinoma cells; hEC cells are human embryonal carcinoma cells
ECM—Extracellular Matrix
ED Cells—Embryo-derived cells; hED cells are human ED cells
EDTA—Ethylenediamine tetraacetic acid
EG Cells—Embryonic germ cells; hEG cells are human EG cells
EP Cells—Embryonic progenitor cells are cells derived from primordial stem cells that are more differentiated than primordial stem cells, in that they no longer display markers such as SSEA4, TRA1-60 or TRA-1-81 seropositivity in the case of the human species, but have not fully differentiated. Embryonic progenitor cells correspond to the embryonic stages as opposed to the postnatal stage of development.
ES Cells—Embryonic stem cells; hES cells are human ES cells
FACS—Fluorescence activated cell sorting
FBS—Fetal bovine serum
GMP—Good Manufacturing Practices
hED Cells—Human embryo-derived cells
hEG Cells—Human embryonic germ cells are stem cells derived from the primordial germ cells of fetal tissue.
hEP Cells—Human embryonic progenitor cells are embryonic progenitor cells from the human species.
hiPS Cells—Human induced pluripotent stem cells are cells with properties similar to hES cells obtained from somatic cells after exposure to hES-specific transcription factors such as SOX2, KLF4, OCT4, MYC, or NANOG, LIN28, OCT4, and SOX2.
HSE—Human skin equivalents are mixtures of cells and biological or synthetic matrices manufactured for testing purposes or for therapeutic application in promoting wound repair.
ICM—Inner cell mass of the mammalian blastocyst-stage embryo.
iPS Cells—Induced pluripotent stem cells are cells with properties similar to hES cells obtained from somatic cells after exposure to ES-specific transcription factors such as SOX2, KLF4, OCT4, MYC, or NANOG, LIN28, OCT4, and SOX2.
LOH—Loss of Heterozygosity
MEM—Minimal essential medium
NT—Nuclear Transfer
PBS—Phosphate buffered saline
PS fibroblasts—Pre-scarring fibroblasts are fibroblasts derived from the skin of early gestational skin or derived from ED cells that display a prenatal pattern of gene expression in that they promote the rapid healing of dermal wounds without scar formation.
RA—Retinoic acid
RFU—Relative Fluorescence Units
SCNT—Somatic Cell Nuclear Transfer
SFM—Serum-Free Medium
SPF—Specific Pathogen-Free
SV40—Simian Virus 40
Tag—Large T-antigen
T-EDTA—Trypsin EDTA

DEFINITIONS

The term "analytical reprogramming technology" refers to a variety of methods to reprogram the pattern of gene expression of a somatic cell to that of a more pluripotent state, such as that of an iPS, ES, ED, EC or EG cell, wherein the reprogramming occurs in multiple and discrete steps and does not rely simply on the transfer of a somatic cell into an oocyte and the activation of that oocyte (see U.S. application No. 60/332,510, filed Nov. 26, 2001; Ser. No. 10/304,020, filed Nov. 26, 2002; PCT application no. PCT/US02/37899, filed Nov. 26, 2003; U.S. application No. 60/705,625, filed Aug. 3, 2005; U.S. application No. 60/729,173, filed Aug. 20, 2005; U.S. application No. 60/818,813, filed Jul. 5, 2006, PCT/US06/30632, filed Aug. 3, 2006, the disclosure of each of which is incorporated by reference herein).

The term "blastomere/morula cells" refers to blastomere or morula cells in a mammalian embryo or blastomere or morula cells cultured in vitro with or without additional cells including differentiated derivatives of those cells.

The term "cell expressing gene X", "gene X is expressed in a cell" (or cell population), or equivalents thereof, means that analysis of the cell using a specific assay platform provided a positive result. The converse is also true (i.e., by a cell not expressing gene X, or equivalents, is meant that analysis of the cell using a specific assay platform provided a negative result). Thus, any gene expression result described herein is tied to the specific probe or probes employed in the assay platform (or platforms) for the gene indicated.

The term "cell line" refers to a mortal or immortal population of cells that is capable of propagation and expansion in vitro.

The term "cellular reconstitution" refers to the transfer of a nucleus of chromatin to cellular cytoplasm so as to obtain a functional cell.

The term "clonal" refers to a population of cells obtained the expansion of a single cell into a population of cells all derived from that original single cells and not containing other cells.

The term "colony in situ differentiation" refers to the differentiation of colonies of cells (e.g., hES, hEG, hiPS, hEC or hED) in situ without removing or disaggregating the colonies from the culture vessel in which the colonies were propagated as undifferentiated stem cell lines. Colony in situ differentiation does not utilize the intermediate step of forming embryoid bodies, though embryoid body formation or other aggregation techniques such as the use of spinner culture may nevertheless follow a period of colony in situ differentiation.

The term "cytoplasmic bleb" refers to the cytoplasm of a cell bound by an intact or permeabilized but otherwise intact plasma membrane, but lacking a nucleus.

The term "differentiated cells" when used in reference to cells made by methods of this invention from pluripotent stem cells refer to cells having reduced potential to differentiate when compared to the parent pluripotent stem cells. The differentiated cells of this invention comprise cells that could differentiate further (i.e., they may not be terminally differentiated).

The term "direct differentiation" refers to process of differentiating: blastomere cells, morula cells, ICM cells, ED cells, or somatic cells reprogrammed to an undifferentiated state (such as in the process of making iPS cells but before such cells have been purified in an undifferentiated state) directly without the intermediate state of propagating isolated undifferentiated stem cells such as hES cells as undifferentiated cell lines. A nonlimiting example of direct differentiation would be the culture of an intact human blastocyst into culture and the derivation of ED cells without the generation of a human ES cell line as was described (Bongso et al, 1994. Human Reproduction 9:2110).

The term "embryonic stem cells" (ES cells) refers to cells derived from the inner cell mass of blastocysts, blastomeres, or morulae that have been serially passaged as cell lines while maintaining an undifferentiated state (e.g. expressing TERT, OCT4, and SSEA and TRA antigens specific for ES cells of the species). The ES cells may be derived from fertilization of an egg cell with sperm or DNA, nuclear transfer, parthenogenesis, or by means to generate hES cells with hemizygosity or homozygosity in the MHC region. While ES cells have historically been defined as cells capable of differentiating into all of the somatic cell types as well as germ line when transplanted into a preimplantation embryo, candidate ES cultures from many species, including human, have a more flattened appearance in culture and typically do not contribute to germ line differentiation, and are therefore called "ES-like cells." It is commonly believed that human ES cells are in reality "ES-like", however, in this application we will use the term ES cells to refer to both ES and ES-like cell lines.

The term "histotypic culture" refers to cultured cells that are aggregated to create a three-dimensional structure with tissue-like cell density such as occurs in the culture of some cells over a layer of agar or such as occurs when cells are cultured in three dimensions in a collagen gel, sponge, or other polymers such as are commonly used in tissue engineering.

The term "human embryo-derived" ("hED") cells refers to blastomere-derived cells, morula-derived cells, blastocyst-derived cells including those of the inner cell mass, embryonic shield, or epiblast, or other totipotent or pluripotent stem cells of the early embryo, including primitive endoderm, ectoderm, mesoderm, and neural crest and their derivatives up to a state of differentiation correlating to the equivalent of the first eight weeks of normal human development, but excluding cells derived from hES cells that have been passaged as cell lines (see, e.g., U.S. Pat. Nos. 7,582,479; 7,217,569; 6,887,706; 6,602,711; 6,280,718; and 5,843,780 to Thomson). The hED cells may be derived from preimplantation embryos produced by fertilization of an egg cell with sperm or DNA, nuclear transfer, or chromatin transfer, an egg cell induced to form a parthenote through parthenogenesis, analytical reprogramming technology, or by means to generate hES cells with hemizygosity or homozygosity in the HLA region. The term "human embryonic germ cells" (hEG cells) refer to pluripotent stem cells derived from the primordial germ cells of fetal tissue or maturing or mature germ cells such as oocytes and spermatogonial cells, that can differentiate into various tissues in the body. The hEG cells may also be derived from pluripotent stem cells produced by gynogenetic or androgenetic means, i.e., methods wherein the pluripotent cells are derived from oocytes containing only DNA of male or female origin and therefore will comprise all female-derived or male-derived DNA (see U.S. application No. 60/161,987, filed Oct. 28, 1999; Ser. No. 09/697,297, filed Oct. 27, 2000; Ser. No. 09/995,659, filed Nov. 29, 2001; Ser. No. 10/374,512, filed Feb. 27, 2003; PCT application no. PCT/US/00/29551, filed Oct. 27, 2000; the disclosures of which are incorporated herein in their entirety).

The term "human embryonic stem cells" (hES cells) refers to human ES cells.

The term "human iPS cells" refers to cells with properties similar to hES cells, including the ability to form all three germ layers when transplanted into immunocompromised mice wherein said iPS cells are derived from cells of varied somatic cell lineages following exposure to de-differentiation factors, for example hES cell-specific transcription factor combinations: KLF4, SOX2, MYC, and OCT4 or SOX2, OCT4, NANOG, and LIN28. Any convenient combination of de-differentiation factors may be used to produce iPS cells. Said iPS cells may be produced by the expression of these genes through vectors such as retroviral, lentiviral or adenoviral vectors as is known in the art, or through the introduction of the factors as proteins, e.g., by permeabilization or other technologies. For descriptions of such exemplary methods see: PCT application number PCT/US2006/030632, filed on Aug. 3, 2006; U.S. application Ser. No. 11/989,988; PCT Application PCT/US2000/018063, filed on Jun. 30, 2000; U.S. application Ser. No. 09/736,268 filed on Dec. 15, 2000; U.S. application Ser. No. 10/831,599, filed Apr. 23, 2004; and U.S. Patent Publication 20020142397 (application Ser. No. 10/015,824, entitled "Methods for Altering Cell Fate"); U.S. Patent Publication 20050014258 (application Ser. No. 10/910,156, entitled "Methods for Altering Cell Fate"); U.S. Patent Publication 20030046722 (application Ser. No. 10/032,191, entitled "Methods for cloning mammals using reprogrammed donor chromatin or donor cells"); and U.S. Patent Publication 20060212952 (application Ser. No. 11/439,788, entitled "Methods for cloning mammals using reprogrammed donor chromatin or donor cells") all of which are incorporated herein by reference in their entirety.

The term "ICM cells" refers to the cells of the inner cell mass of a mammalian embryo or the cells of the inner cell mass cultured in vitro with or without the surrounding trophectodermal cells.

The term "oligoclonal" refers to a population of cells that originated from a small population of cells, typically 2-1000 cells, that appear to share similar characteristics such as morphology or the presence or absence of markers of differentiation that differ from those of other cells in the same culture. Oligoclonal cells are isolated from cells that do not share these common characteristics, and are allowed to proliferate, generating a population of cells that are essentially entirely derived from the original population of similar cells.

The term "organotypic culture" refers to cultured cells that are aggregated to create a three-dimensional structure with tissue-like cell density such as occurs in the culture of some cells over a layer of agar, cultured as teratomas in an animal, otherwise grown in a three dimensional culture system but wherein said aggregated cells contain cells of different cell lineages, such as, by way of nonlimiting examples, the combination of epidermal keratinocytes and dermal fibroblasts, or the combination of parenchymal cells with their corresponding tissue stroma, or epithelial cells with mesenchymal cells.

The term "pluripotent stem cells" is used synonymously with the term "primordial stem cells" as defined below.

The term "pooled clonal" refers to a population of cells obtained by combining two or more clonal populations to generate a population of cells with a uniformity of markers such as markers of gene expression, similar to a clonal population, but not a population wherein all the cells were derived from the same original clone. Said pooled clonal lines may include cells of a single or mixed genotypes. Pooled clonal lines are especially useful in the cases where clonal lines differentiate relatively early or alter in an undesirable way early in their proliferative lifespan.

The term "primordial stem cells" refers to animal cells capable of differentiating into more than one differentiated cell type. Such cells include hES cells, blastomere/morula cells and their derived hED cells, hiPS cells, hEG cells, hEC cells, and adult-derived cells including mesenchymal stem cells, neuronal stem cells, and bone marrow-derived stem cells. Primordial stem cells may be from non-human animals. Primordial stem cells may be genetically modified or not genetically modified. Genetically modified cells may include markers such as fluorescent proteins to facilitate their identification in vitro or in vivo.

DETAILED DESCRIPTION

As summarized above, aspects of the present invention include methods and compositions related to the production, identification and use of embryonic progenitor cell lines that are capable of undergoing chondrogenesis.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Embryonic Chondrogenic Progenitor Cells and Methods of Use

Aspects of the present invention include methods and compositions related to the production, identification and use of embryonic progenitor cells that are capable of undergoing chondrogenesis. A diverse set of clonal cell lines that express central regulators of the mesenchyme associated with that of the limb and joint such as MSX1, MSX2, and SOX9-expressing lines with a subset of lines expressing high levels of the joint-specific marker GDF5 have been described (see West et al., 2008, Regenerative Medicine vol. 3(3) pp. 287-308, incorporated herein by reference, including supplemental information; and U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety). These clonally-purified lines are robust, are able to expand for >40 passages while maintaining their pattern of gene expression, have not demonstrated tumorigenicity, and have an embryonic pattern of gene expression. These lines thus provide for compositions and methods of producing diverse cartilage types with unique molecular compositions for use in research and therapy.

In certain embodiments, the gene expression pattern of the undifferentiated embryonic chondrocyte progenitor cells or cell lines of the present invention provides no indication that they have the potential to become chondrocytes under the appropriate culture conditions. In other words, the cells do not have a gene expression pattern indicative of chondrocyte developmental potential.

Certain of the chondrogenic embryonic progenitor cell lines of the present invention, when induced under chondrogenic conditions, are capable of generating cartilage without expressing COL10A1 or the IHH gene, both of which are expressed in MSCs under such conditions and are markers of hypertrophic chondrocytes. Hypertrophic chondrocytes provide a temporary matrix that is later invaded by osteoblasts to make bone, and thus are not suited for certain therapeutic purposes (e.g., when injected into the joint, or otherwise transplanted into articular cartilage, in an effort to regenerate that tissue for the treatment of joint cartilage trauma, arthritis, or related uses). Therefore, the cell lines of the present invention have important therapeutic differences from other chondrocyte progenitors that develop into hypertrophic chondrocytes (e.g., bone marrow-derived MSC).

Exemplary embryonic chondrocyte progenitor cells according to the present invention are negative for the expression of any one, two, three, four or all of the following genes: CD74, CD90, CD166, ITGA2, and KCNK2. Each of these genes are markers present in mesenchymal stem cells (MSCs), which are currently in use in cartilage replacement therapy (described further below). Thus, the chondrogenic embryonic progenitor cell lines of the present invention have gene expression patterns that are distinct from other known chondrogenic progenitor cells. In certain embodiments, chondrogenic embryonic progenitor cells are further negative for the expression of HOX genes and PITX1.

Below is a list of exemplary human embryonic chondrocyte progenitor cell lines according to aspects of the present invention and certain gene expression markers of interest (positive and negative markers). These human embryonic chodrocyte progenitor cell lines are capable of differentiating into chondroblasts and then chondrocytes expressing higher levels of COL2A1 than normal early passage cultured human articular chondrocytes (NHACs) when they have undergone 18-21 doublings of clonal expansion following isolation from human ES or similar human primordial stem cell-derived cells.

Gene expression markers of the cell line MEL2 in the range of P22-28 can be determined by comparing the gene expression pattern of the cells in the undifferentiated (Control or Ctrl)) state as shown in Table 1. Specific gene expression markers expressed by the cell line include the genes: PIP, ENPP2, DLX5, CXADR, NPTX2, CLDN23, SFRP2, HSPB3, HAND2, HSD17B2, RCAN2, EBF3, GPM6B, RNF175, PPARGC1A, RGS16, GPM6B, SOX17, EPHB6, and BAPX1. The most specific of these markers being expressed in the cell line MEL2 in the range of P22-28 are: PIP (Illumina probe ID 4010519), SOX17 (Illumina probe ID 3610193), DLX5 (Illumina probe ID 3370767), GPM6B (Illumina probe ID 2630279), RGS16 (Illumina probe ID 1030102), EPHB6 (Illumina probe ID 7400017), and HAND2 (Illumina probe ID 4640563) and negative expression of: TBX15 (Illumina probe ID 6060113), HOXA2 (Illumina probe ID 2060471), AJAP1 (Illumina ID 1300647), and HOXB2 (Illumina probe ID 3460097).

Gene expression markers of the cell line SM30 in the range of P13-15 can be determined by comparing the gene expression pattern of the cells in the undifferentiated (Control or Ctrl)) state as shown in Table 1. Specific gene expression markers expressed by the cell line include the genes: COL15A1, DYSF, FST, ITGB4, TMEM119, MSX1, NDST3, NTRK1, and ZIC2. The most specific of these gene expression markers being expressed in cell line SM30 in the range of P13-15 are: NTRK1 (Illumina probe ID 7050113), NDST3 (Illumina probe ID 670537), ZIC2 (Illumina probe ID 510368), ITGB4 (Illumina probe ID 3940132), and negative expression of PIP (Illumina probe ID 4010519), NNAT (Illumina probe ID 4010709), HOXA2 (Illumina probe ID 2060471), TBX15 (Illumina probe ID 6060113), and HAND2 (Illumina probe ID 4640563).

Gene expression markers of the cell line 7SMOO32 in the range of P11-18 can be determined by comparing the gene expression pattern of the cells in the undifferentiated (Control or Ctrl)) state as shown in Table 1. Specific gene expression markers expressed by the cell line include the genes: EGFL6, FGF13, BEX2, CHRNA3, NCAM2, BBOX1, and DLK1. The most specific of these gene expression markers being expressed in 7SMOO32 are: EGFL6 (Illumina probe ID 6330079), FGF13 (Illumina probe ID 7380239), CHRNA3 (Illumina probe ID 4280180), BBOX1 (Illumina probe ID 3400386), and negative for the expression of the genes: TBX15 (Illumina probe ID 6060113), NNAT (Illumina probe ID 4010709), NTRK1 (Illumina probe ID 7050113), HAND2 (Illumina probe ID 4640563), and HOXA2 (Illumina probe ID 2060471).

Gene expression markers of the cell line SK11 in the range of P12-17 can be determined by comparing the gene expression pattern of the cells in the undifferentiated (Control or Ctrl)) state as shown in Table 1. Specific gene expression markers expressed by the cell line include the genes: PITX1, TBX15, NCAM1, COL21A1, CYYR1, LAMP3, MEGF10, RNF165 and GDF10. The most specific of these gene expression markers being expressed in SK11 are: TBX15 (Illumina probe ID 6060113), COL21A1 (Illumina probe ID 3440747), GDF10 (Illumina probe ID 5690095), PITX1 (Illumina probe ID 2000373), and negative for the expression of the genes: NNAT (Illumina probe ID 4010709), HAND2 (Illumina probe ID 4640563), FOXF2 (Illumina probe ID 1660470), FOXG1 (Illumina probe ID 4200458), HOXA2 (Illumina probe ID 2060471) HOXB2 (Illumina probe ID 3460097), and AJAP1 (Illumina ID 1300647).

Gene expression markers of the cell line 7PEND24 in the range of P15-26 can be determined by comparing the gene expression pattern of the cells in the undifferentiated (Control or Ctrl)) state as shown in Table 1. Specific gene expression markers expressed by the cell line include the genes: TBX15, CA9, SPAG16, SUSD2, TBXAS1, AIF1, SLITRK5, FOXF2, AADAC, and FOXG1. The most specific of these gene expression markers being expressed in 7PEND24 are: AADAC (Illumina probe ID 6200619), TBX15 (Illumina probe ID 6060113), SPAG16 (Illumina probe ID 4390537), AIF1 (Illumina probe ID 3800047), and negative for the expression of the genes: NNAT (Illumina probe ID 4010709), PITX1 (Illumina probe ID 2000373), SOX17 (Illumina probe ID 3610193), and AJAP1 (Illumina ID 1300647).

Gene expression markers of the cell line E15 in the range of P14-15 can be determined by comparing the gene expression pattern of the cells in the undifferentiated (Control or Ctrl)) state as shown in Table 1. Specific gene expression markers expressed by the cell line include the genes: ENPP2, ABCA6, TBX15, BAI3, CNTN3, TSPYL5, GAP43, AJAP1, CYFIP2, HOXA2 (Illumina probe ID 2060471) HOXB2 (Illumina probe ID 3460097), and NNAT. The most specific of these gene expression markers being expressed in E15 are: AJAP1 (Illumina probe ID 1300647), BAI3 (Illumina probe ID 5690301), NNAT (Illumina probe ID 4010709), ABCA6 (Illumina probe ID 5810209), and negative for the expression of the gene: PITX1 (Illumina probe ID 2000373) and is negative for the gene expression markers: HAND2 (Illumina probe ID 4640563) and SOX17 (Illumina probe ID 3610193).

Gene expression markers of the cell line 4D20.8 in the range of P12-17 can be determined by comparing the gene expression pattern of the cells in the undifferentiated (Control or Ctrl)) state as shown in Table 1. Specific gene expression markers expressed by the cell line include the genes: LHX8, HAPLN1, LINGO2, FGF18, GPR126, BBOX1, ITGA4, SHISA3, and BARX1 and is negative for the gene expression markers: NNAT and HAND2. The most specific of these gene expression markers being expressed in 4D20.8 are: SHISA3 (Illumina probe ID 5670286), LHX8 (Illumina probe ID 2900343), BARX1 (Illumina probe ID 6450040), LINGO2 (Illumina probe ID 1110291), and negative for the expression of the genes: PITX1 (Illumina probe ID 2000373), SOX17 (Illumina probe ID 3610193), and AJAP1 (Illumina ID 1300647).

As noted above, the embryonic chondrocyte progenitor cells of the present invention find use in methods for generating cartilage in vitro or in vivo (sometimes referred to herein as chondrocyte induction methods). Any convenient chondrocyte induction method may be used, including those suitable for therapeutic use (a number of exemplary chondrocyte induction/cartilage generation methods are described below and in the Examples section).

Thus, the embryonic chondrocyte progenitor cells of the present invention may be used in therapeutic applications for the repair of cartilage tissue. administered to a subject, e.g., in a therapeutically acceptable carrier. The subject to which the progenitor cells are administered may have any condition, injury or disease for which cartilage replacement/regeneration would provide a therapeutic benefit. For example, if a subject has cartilage damage at a specific site, e.g., articular cartilage damage, the embryonic progenitor cell line may be administered to the site of the cartilage damage. Pharmaceutically acceptable carriers for such treatments include any of a wide variety of scaffolds, matrices and the like that find use as therapeutic carriers for cell transplantation. Non limiting examples include carriers that contain any one or combination of the following components: Hextend; hyaluronan and polymers thereof; chondroitin sulfate; type I collagen; type II collagen; type III collagen, polyanhydride, polyorthoester, polyglycolic acid and copolymers thereof; alginate; agarose; polaxomers; fibrin; chitin; and chitosan. Exemplary scaffolds/matrices and their use in chondrocyte differentiation and therapies are described in further detail below.

In certain therapeutic applications, the chondrocyte embryonic progenitor cell line employed may be cultured under chondrocyte inducing conditions prior to administering the cells to the subject, e.g., to induce cartilage production prior to transplantation. For example, a form or other structure containing cartilage generated from a line of the present invention (e.g., molded structure) may be transplanted into a subject, e.g., at the site of cartilage loss, injury or degeneration. Any convenient cartilage producing condition may be employed in such embodiments, including any one or combination of: chondrocyte culture conditions; impregnating the embryonic progenitor cell line into synthetic matrices or biological resorbable immobilization vehicles; and placing the embryonic progenitor cell line into a molded structure.

Methods of treatment according to the present invention may also include measuring the rate of generation of cartilage at the desired site (e.g., measuring the repair or replacement of the damaged cartilage) at one or more time points after transplantation as well as obtaining information as to the performance of the newly formed cartilage in the subject. Parameters measured can include the survival, localization, and number of administered cells present at the transplantation site in the patient. The degree cell engraftment or reconstitution may be determined using any of a variety of scanning techniques, e.g., computerized axial tomography (CAT or CT) scan, magnetic resonance imaging (MRI) or positron emission tomography (PET) scans. Functional integration of transplanted cells according to the invention into a subject can be assessed by examining restoration of the function that was damaged or diseased, for example, restoration of joint, or augmentation of function. Cell transplant engraftment, localization and survival can also be done by removing the target tissue, and examining it visually or through a microscope (e.g., in post mortem analysis).

Tissue Engineered Cartilage

Three types of cartilage are present in a mammal and include: hyaline cartilage; fibrocartilage and elastic cartilage. Hyaline cartilage consists of a gristly mass having a firm, elastic consistency, is translucent and is pearly blue in color. Hyaline cartilage is predominantly found on the articulating surfaces of articulating joints. It is found also in epiphyseal plates, costal cartilage, tracheal cartilage, bronchial cartilage and nasal cartilage. Fibrocartilage is essentially the same as hyaline cartilage except that it contains fibrils of type I collagen that add tensile strength to the cartilage. The collagenous fibers are arranged in bundles, with the cartilage cells located between the bundles. Fibrocartilage is found commonly in the anulus fibrosus of the invertebral disc, tendonous and ligamentous insertions, menisci, the symphysis pubis, and insertions of joint capsules. Elastic cartilage also is similar to hyaline cartilage except that it contains fibers of elastin. It is more opaque than hyaline cartilage and is more flexible and pliant. These characteristics are defined in part by the elastic fibers embedded in the cartilage matrix. Typically, elastic cartilage is present in the pinna of the ears, the epiglottis, and the larynx.

In certain embodiments, cartilage-producing cells of the present invention are employed in therapeutic applications to repair, replace, or enhance cartilage tissue (e.g., damaged cartilage) in a subject (e.g., a mammal, e.g., a human patient). The cartilage may be generated in vitro followed by transplantation to the affected site or, in certain embodiments, chondrocytes may be transplanted (e.g., within a matrix or scaffold) to produce cartilage at the desired site in the subject. A number of therapies that employ cartilage-producing cells (or chondrocytes) have been described, a few of which are summarized below.

In certain embodiments, synthetic matrices or biological resorbable immobilization vehicles (sometimes referred to as "scaffolds" or "matrices") may be impregnated with cartilage-producing cells of the present invention. A variety of synthetic carrier matrices have been used to date and include: three-dimensional collagen gels (U.S. Pat. No. 4,846,835; Nishimoto (1990) Med. J. Kinki University 15; 75-86; Nixon et al. (1993) Am. J. Vet. Res. 54:349-356; Wakitani et al. (1989) J. Bone Joint Surg. 71B:74-80; Yasui (1989) J. Jpn. Ortho. Assoc. 63:529-538); reconstituted fibrin-thrombin gels (U.S. Pat. Nos. 4,642,120; 5,053,050 and 4,904,259); synthetic polymer matrices containing polyanhydride, polyorthoester, polyglycolic acid and copolymers thereof (U.S. Pat. No. 5,041,138); and hyaluronic acid-based polymers (Robinson et al. (1990) Calcif. Tissue Int. 46:246-253). Certain of these scaffolds and matrices are being used in (or being tested for) therapeutic cartilage repair, including collagen type 1 matrices (e.g., Atelocollagen from Koken Co Ltd, Tokyo Japan); collagen type I and III bilayer scaffolds (e.g., from Verigen, Leverkusen, Germany); collagen scaffolds (e.g., covered Autologous Chondrocyte Implantation (CACI) and matrix-induced autologous chondrocyte implantation (MACI) systems (ACI-Maix™) from Matricel, Hezoenrath, Germany); procine type I/type III collagen bilayer (e.g., ChondroGide® (Geistlich Biomaterials, Wolhusen, Switzerland); 3D-Collagen-Gel-Matrices (e.g., as used in CaReS® from BioRegioSTERN, Friedrichstraβe, Stuttgart and Arthro Kinetics Inc, Boston, Mass.); hyaluruanan scaffold, e.g., esterified (benzyl ester) derivative of hyaluranan based biodegradable polymer (e.g., Hyaff®-11 from Fida Advanced Biopolymers Laboratories, Abano Terme, Italy); PGA/PLA copolymer and polydioxanone scaffold, e.g., a gel-loaded porous biodegradable fleece (e.g., as employed in Bio-Seed-C from Biotissue Technologies, Freiburg, Germany); solid scaffolds with agarose-alginate matrix (e.g., Cartipatch® from TBF Tissue Engineering, MIONS, FRANCE); biphasic, three-dimensional collagen-chondroitin sulfate scaffolds (e.g., NOVOCART™3D from TETEC, Reutlingen, Germany).

The cartilage-producing cells of the present invention may be employed in cartilage reconstruction as described in Methods of Tissue Engineering (2002), edited by Anthony Atala and Robert P. Lanza and published by Academic Press (London), incorporated by reference herein for its description of cartilage reconstruction (see, e.g, pages 1027 to 1039). As described therein, cartilage-producing cells may be placed into a molded structure (e.g., by injection molding) and transplanted into an animal. Over time, cartilage produced by the cartilage-producing cells will replace the molded structure, thereby producing a formed cartilage structure (i.e., in the shape of the initial molded structure). Exemplary mold materials for the molded structure include hydrogels (e.g., alginate, agarose, polaxomers (Pluronics)) and natural materials (e.g., type I collagen, type II collagen, and fibrin).

In certain embodiments, cartilage-producing cells of the present invention may be cultured in vitro to form a synthetic cartilage (or cartilage-like) material. The resulting cartilage may be implanted subsequently into a subject at the site of the cartilage defect. This type of approach has the advantage that the development of the synthetic cartilage material may be monitored prior to implantation. In addition, the resulting cartilage may be characterized biochemically and morphologically prior to implantation. Two general procedures have been developed for growing synthetic cartilage in vitro. These include growing cartilage producing cells in either an anchorage-dependent or an anchorage-independent manner.

In the anchorage-independent manner, the cartilage-producing cells may be cultured as colonies within an agarose gel. See for example: Benya et al. (1982) Cell 30:215-224; Aydlotte et al. (1990) in Methods and Cartilage Research Chapter 23: pp. 90-92; Aulthouse et al. (1989) In Vitro Cellular and Developmental Biology 25:659-668; Delbruck et al. (1986) Connective Tissue Res. 15:1550-172; and Bohme et al. (1992) J. Cell Biol. 116:1035-1042. Alternatively, in another anchorage-independent method, cartilage-producing cells may be cultured as colonies in suspension culture. See for example, Franchimont et al. (1989) J. Rheumatol. 16:5-9; and Bassleer et al. (1990) in "Methods and Cartilage Research", Academic Press Ltd., Chapter 24.

In the anchorage-dependent method, primary cultures of cartilage-producing cells may be grown as monolayers attached to the surface of a cell culture flask. See for example: Yoshihashi (1983) J. Jpn. Ortho. Assoc. 58:629-641; and U.S. Pat. No. 4,356,261, incorporated by reference herein in its entirety.

In certain embodiments, a cartilage therapy of the invention includes those described in U.S. Pat. Nos. 5,723,331 and 5,786,217 (entitled "Methods and compositions for the repair of articular cartilage defects in mammals", both of which are incorporated by reference herein in their entirety). These patents describe methods for preparing in vitro a synthetic cartilage patch for the repair of a cartilage defect. When the cartilage-producing cells of the present invention are employed, the methods include the steps of: (1) seeding cartilage-producing cells of the present invention into a preshaped well having a cell contacting, cell adhesive surface; and (2) culturing the cartilage-producing cells of the present invention in the well for a time sufficient to permit the cells to secrete an extracellular matrix, thereby to form a three-dimensional, multi cell-layered patch of synthetic cartilage. The resulting synthetic cartilage (e.g., synthetic articular cartilage), contains cartilage-producing cells of the present invention dispersed within an endogenously produced and secreted extracellular matrix. The resulting synthetic cartilage patch may be used subsequently for the repair (or replacement) of a cartilage defect in a subject (e.g., a mammal).

As another example, the chondrogenic cells of the present invention may be encapsulated in three dimensional matrices, e.g., hydrogels. Exemplary hydrogel encapsulation methods can be found in "Directed Differentiation of Embryonic Stem Cells in Three-Dimensional Hydrogel Culture", Nathaniel S. Hwang, Shyni Varghese, and Jennifer Elisseeff, Methods in Molecular Biology, vol. 407: p 351 Stem Cell Assays, incorporated herein by reference. Exemplary processes described therein are summarized below.

A. Photo-Encapsulation of Chondrocyte Progenitors in PEGDA or RGD-Modified PEGDA Hydrogels 1. Prepare PEGDA polymer Poly(ethylene glycol)-diacrylate (PEGDA; cat. no. 01010F12, Nektar, Huntsville, Ala., USA) solution or RGD-modified PEGDA polymer solution by mixing the macromer at 10% (w/v) in sterile PBS. Protect the polymer solution from light and that can be stored at −20° C. for 3 months.

2. Dissolve 100 mg of photo-initiator, Igracure 2959 (Product No. 1706673, Ciba Specialty Chemicals, Tarrytown, N.Y., USA), in 1 ml of 70% filter-sterilized ethanol.

3. Place both the PEGDA solution and the photo-initiator solution over crushed ice until their usage.

5. Add the photo-initiator to the PEGDA solution and mix thoroughly to make a final concentration of 0.05% (w/v). Make sure that the initiator is mixed very well with the macromer solution (5 ul of photo-initiator solution/ml of polymer solution).

6. Suspend the cells (20-30 million/ml) within the precursor (polymer with photoinitiator) solution by adding the PEGDA solution containing photo-initiator into a cell pellet and mix thoroughly using a pipette without creating bubbles.

7. Transfer 100_1 of progenitor cell-polymer solution to cylindrical mold and expose to longwave, 365 nm light at 4.4 mW/cm$^2$ (Glowmark System, Upper Saddle River, N.J., USA), for 5 min to complete gel formation.

8. Remove the "solidified" chondrocyte progenitor cell-laden hydrogels from their mold and transfer them to 12-well plates with chondrogenic medium containing 10 ng/ml TGF-β1 and incubate at 37° C. and 5% $CO_2$. Change medium every 2-3 days.

B. Encapsulation of Chondrocyte Progenitors in Alginate Hydrogel

1. Collect the chondrogenic cells in a 50-ml conical tube and centrifuge for 5 min at 145 g. Remove the supernatant and add the alginate polymer or RGD-modified alginate polymer solutions and gently suspend the cells using a (P-1000) Pipetteman. Avoid making bubbles in the liquid.

2. Take one of the Transwell tissue culture insert trays and fill the well with 1 ml of calcium chloride solution.

3. Using a Pipetteman, add 100 ul of the cell suspension to the tissue culture inserts. After all the inserts are filled, use sterile forceps to transfer the inserts into the wells containing calcium chloride solution. Incubate them at 37° C. for 20 min in 5% $CO_2$.

4. Remove the constructs from the inserts using gentle prying motion with a thin, curved spatula. Place one construct in each well and incubate at 37° C. at 5% $CO_2$.

The hydrogel encapsulated chondrocyte progenitor cells can be cultured in vitro or transplanted in vivo to a site for which cartilage production is desired, e.g., to replace damaged or missing cartilage.

Glycosan Biosystems also provide hydrogels for 3 dimensional cell culture that find use in culture, tissue engineering scaffolds, and cell therapy. This company provides, for example, hyaluuronan-based, PEG-based, and collagen-based hydrogels for use in in vitro and in vivo cell growth and differentiation.

One examplary hydrogel system from Glycosan Biosystems is HyStem-CSS™, which allows gentle and quick recovery of encapsulated cells in 3-D cultures. HyStem-CSS uses a novel crosslinker, PEGSSDA, which allows for liquefaction of the HyStem-C hydrogel using only small amounts of reducing agent. Reconstituted HyStem-CSSTM components remain liquid at 15 to 37° C. The hydrogel is formed when the crosslinking agent, PEGSSDA is added to a mixture of Glycosil™ (thiol-modified hyaluronan) and Gelin-S™

(thiol-modified gelatin). Gelation occurs in about twenty minutes after all three components are mixed. No steps depend on low temperatures or low pH. Diluting the components with phosphate-buffered saline (PBS) or cell-culture medium can increase the gelation time. The resulting hydrogel can be disolved in 40 ml of acetyl-L-cysteine (reducing agent) in less than 2 hours at 37° C.

According the the manufactures protocol, HyStem-CSS hydrogels (3×2.5 ml=7.5 mL) is prepared as follows:

Allow the HyStem, Gelin-S, PEGSSDA, and DG Water vials to come to room temperature.

Under aseptic conditions, using a syringe and needle, add 1.0 mL of DG Water to the HyStem vial. Repeat for the Gelin-S vial.

Place both vials horizontally on a rocker or shaker. It will take <30 minutes for the solids to fully dissolve. Warming to not more than 37° C. and/or gently vortexing will speed dissolution, Solutions will be clear and slightly viscous.

Under aseptic conditions, using a syringe and needle, add 0.5 mL of DG Water to the PEGSSDA vial. Invert several times to dissolve.

As soon as possible, but within 2 hours of making the solutions, aseptically mix equal volumes of HyStem and Gelin-S™. To mix, pipette back and forth slowly to avoid trapping air bubbles.

Resuspend cell pellet in 2.0 mL of HyStem+Gelin-S. Pipette back and forth to mix.

To form the hydrogel, add PEGSSDA to the HyStem+Gelin-S mix in a 1:4 volume ratio (0.5 mL PEGSSDA™ to 2.0 mL HyStem+Gelin-S) and mix by pipette.

Allow solution to react for 10 minutes then mix again by pipette to ensure even distribution of cells. Gelation will occur within ~10 to 20 minutes.

Another exemplary scaffold that finds use in chondrogenesis applications is decellularized tissues, for example from cadaveric sources, e.g., human cadeveric tissue. (See, e.g., Minehara et al., "A new technique for seeding chondrocytes onto solvent-preserved human meniscus using the chemokinetic effect of recombinant human bone morphogenetic protein-2." Cell Tissue Bank. 2010 Jun. 17. [Epub ahead of print]; Yang et al. "A cartilage ECM-derived 3-D porous acellular matrix scaffold for in vivo cartilage tissue engineering with PKH26-labeled chondrogenic bone marrow-derived mesenchymal stem cells." Biomaterials. 2008 May; 29(15): 2378-87; and Stapleton et al., "Development and characterization of an acellular porcine medial meniscus for use in tissue engineering." Tissue Eng Part A. 2008 April; 14(4): 505-18; each of which are incorporated herein by reference).

For example, Minehara et al describe a chemotactic cell seeding technique using solvent-preserved human meniscus from cadavers and a chondrocyte chemotactic agent. Minehara demonstrate that rhBMP-2 (at 10 ng/ml) is able to induce chondrocytes to migrate into a decellularized human meniscus. Minehara et al. showed that after a 3-week incubation, newly-formed cartilaginous extracellular matrix was synthesized by migrated chondrocytes throughout the meniscus, down to a depth of 3 mm.

Direct Injection of Cells to Impart In Situ Chondrogenesis

Direct injection of cells, such as the cell lines 4D20.8, MEL2, 7SMOO32, SM30, SK11, 7PEND24, or E15, or human or animal cells with the same or analogous markers or other cells of the present invention, are also of therapeutic utility similar to that previously reported with adult bone marrow-derived MSCs (Chondrogen). Patients undergo meniscectomy followed by a single injection of either hyaluronic acid (HA) or a low dose (50 million cells) or high dose (150 million cells) of MSCs. Patients are monitored for safety and additional preliminary efficacy such as pain, cartilage damage, and tissue repair for two years. Non-invasive MRI is used for examination of meniscus and cartilage condition. In patients with osteoarthritis (OA) at the time of surgery, a statistically significant 20 mm reduction in pain, as measured by the visual analog scale (VAS), was observed in patients receiving a single injection of MSCs over patients receiving an injection of the control, HA, at one year (MSCs 48 mm vs. Control 28 mm, p=0.05). The reduction in pain increased even further to 37 mm with more severe osteoarthritic changes in the patient's joint (p=0.004, MSCs 56 mm vs. Control 19 mm). For comparison, currently available treatments for OA, such as HA, were approved by the Food and Drug Administration (FDA) based upon improvements of 9-23 mm over placebo. The MRI volume analysis method was deemed unsuitable for computational analysis because of the high level of variability seen between readings. As a result, no meaningful evaluation of meniscus regeneration can be made. The beneficial effects of adult MSCs were also seen in physical measures of joint condition. Bony changes associated with osteoarthritis, such as subchrondral sclerosis and osteophyte formation, were reported in 21% of patients receiving the control, but only 6% of MSC-treated patients. There was also a positive dose-response effect. At one year, the improvement in pain relative to baseline, prior to surgery to remove damaged meniscus, was 56 mm for high dose MSCs, 26 mm for low dose, and 19 mm for the control. Cell-based therapy for the joint would benefit from technologies to generate joint-specific and patient-specific stem cells, cells with improved capacity for regenerating joint tissues, cells with improved capacity for scale-up and cryopreservation. The present invention provides cell lines that express SOX9, MSX1, and MSX2 suitable for industrial scale-up.

Methods for the Production of Embryonic Progenitor Cell Lines

In addition to the methods described below, methods that find use in the production and use of the cell lines described herein can be found in the following: U.S. Patent Publication 20080070303, entitled "Methods to accelerate the isolation of novel cell strains from pluripotent stem cells and cells obtained thereby"; U.S. patent application Ser. No. 12/504,630 filed on Jul. 16, 2009 and titled "Methods to Accelerate the Isolation of Novel Cell Strains from Pluripotent Stem Cells and Cells Obtained Thereby"; U.S. provisional application Ser. No. 61/226,237 filed on Jul. 16, 2009 and titled "Methods and Compositions Useful for In Vitro and In Vivo Chondrogenesis Using Embryonic Progenitor Cell Lines"; and PCT Application PCT/US2006/013519, filed on Apr. 11, 2006, entitled "NOVEL USES OF CELLS WITH PRENATAL PATTERNS OF GENE EXPRESSION", each of which is incorporated by reference herein in its entirety.

While the methods below describe the production of embryonic progenitor cell lines from hES cells, other primordial stem cells may be employed, e.g., primordial stem cells from human or non-human animals.

hES Cell Culture and Generation of Candidate Cultures.

The hES cell lines used were previously described H9 (National Institutes of Health-registered as WA09) and the line (MA03) derived at Advanced Cell Technology (West et al., 2008, *Regenerative Medicine* vol. 3(3) pp. 287-308). hES cells were routinely cultured in hES medium (KO-DMEM (Invitrogen, Carlsbad, Calif.), 1× nonessential amino acids (Invitrogen, Carlsbad, Calif.), 1× Glutamax-1 (Invitrogen, Carlsbad, Calif.), 55 uM beta-mercaptoethanol (Invitrogen, Carlsbad, Calif.), 8% Knock-Out Serum Replacement (Invitrogen, Carlsbad, Calif.), 8% Plasmanate, 10 ng/ml LIF (Millipore, Billerica, Mass.), 4 ng/ml bFGF (Millipore, Billerica, Mass.), 50 unit/ml Penicillin—50 units/ml Streptomycin (Invitrogen, Carlsbad, Calif.). The hES cell lines were maintained at 37 deg C. in an atmosphere of 10% CO2 and 5% O2 on Mitomycin-C treated mouse embryonic fibroblasts (MEFs) and passaged by trypsinization or periodic manual selection of colonies. For the production of clonal embryonic progenitors, hES cells were plated at 500-10,000 cells per 15 cm dish and then differentiated under a two-step protocol, the first step being the differentiation of hES cells under an array of conditions to yield diverse heterogeneous cultures of cells called "candidate cultures." The generation of candidate cultures was performed with either adherent hES cells grown on MEFs (colony in situ differentiation) or with hES-derived embryoid bodies (EB). For colony in situ differentiation experiments, hES cells were allowed to grow to confluence and differentiated by a variety of methods (as described in Supplementary Table I from West et al., 2008, *Regenerative Medicine* vol. 3(3) pp. 287-308, which is incorporated by reference herein in its entirety). By way of nonlimiting example, in the case of colony in situ differentiation in DMEM with 10% FCS, culture medium was aspirated from cultures of hES cell colonies on mouse feeders, and the media was replaced with DMEM medium containing 10% FBS for differentiation and after various time periods (1, 2, 3, 4, 5, 7, and 9 days in differentiation medium). The cells were then dissociated with 0.25% trypsin (Invitrogen, Carlsbad, Calif.) and plated in 150 cm$^2$ flasks for expansion. The candidate cells from each time point in the 150 cm$^2$ flasks were plated out for cloning and expansion as described below. For EB differentiation experiments, confluent hES cultures were treated for 15 minutes at 37° C. with 1 mg/ml Collagenase IV (in DMEM, Invitrogen, Carlsbad, Calif.) to release the colonies. The detached, intact colonies were scraped and collected by centrifugation (150×g for 5 minutes), resuspended in differentiation medium described in Supplementary Table I (from West et al., 2008, *Regenerative Medicine* vol. 3(3) pp. 287-308, which is incorporated by reference herein in its entirety) and transferred to a single well of a 6-well Ultra-Low Binding plate (Corning, distributed by Fisher Scientific, Pittsburgh, Pa.) containing the same differentiation medium. The EBs were allowed to differentiate, depending on the experiment, from 4-7 days and the differentiated EBs dissociated with 0.25% trypsin, plated in 6-well plates containing various expansion medium. The candidate cultures in the 6 well plates are allowed to grow to confluence and plated out for cloning and expansion as described below.

Isolation and Expansion of Clonal Cell Lines.

The partially differentiated candidate cell cultures described above were dissociated with 0.25% trypsin to single cells and plated onto duplicate 15 cm gelatin coated plates at cloning densities of approximately 500 and/or 1,000 and/or 2,000 and/or 5,000 cells per plate for further differentiation and expansion in a variety of growth media shown in Supplementary Table I (from West et al., 2008, *Regenerative Medicine* vol. 3(3) pp. 287-308, which is incorporated by reference herein in its entirety). The clonal density cells were allowed to grow, undisturbed, for 10-14 days and colonies that develop were identified and collected with cloning cylinders and trypsin using standard techniques. The cloned colonies were transferred onto gelatin-coated 24 well plates for expansion. As the clones become confluent in the 24 well plates (but without letting the cells remain confluent for more than 2 days), they were sequentially expanded to 12 well, 6 well, T-25 flask, T-75 flask, T-150 or T-225 flasks and, finally, roller bottles. Clonal cell lines that expand to the roller bottle stage are assigned a unique ACTC identification number, photographed and cryopreserved in aliquots for later use.

Once cells reached a confluent 6 well dish, they were passaged to a T-25 flask and a fraction of the cells (5×10$^5$) were removed for plating in a gelatinized 6 cm dish for gene expression profile analysis. Alternatively, some cells were first passaged to T-225 flasks, then a fraction of the cells (5×10$^5$) were removed for plating in a gelatinized 6 cm dish for gene expression profile analysis. The population doublings that the cells had undergone were therefore determined to be 18-21 PDs. Following removal of the cell clones from the cloning plates, remaining colonies were visualized by Crystal violet staining (Sigma HT9132-1L) in 100% ethanol per manufacturer's instructions. Cell Culture media utilized in experiments include: Smooth muscle cell basal medium (Cat#C-22062B) and growth supplement (Cat#C-39267), Skeletal muscle basal medium (Cat#C-22060B) and growth supplement (Cat#C-39365), Endothelial cell basal medium (Cat#C-22221) and growth supplement (Cat#C-39221), Melanocyte cell basal medium (Cat#C-24010B) and growth supplement (Cat#C-39415) were obtained from PromoCell GmbH (Heidelberg, Germany). Epi-Life, calcium free/phenol red free medium (Cat#M-EPIcf/PRF-500) and low serum growth supplement (Cat#S-003-10) were purchased from Cascade Biologics (Portland, Oreg.). Mesencult basal medium (Cat#05041) and supplement (Cat#5402) were obtained from Stem Cell Technologies (Vancouver, BC). Dulbecco's modified Eagle's medium (Cat#11960-069) and Fetal bovine serum (Cat#SH30070-03) were purchased from Invitrogen (Carlsbad, Calif.) and Hyclone (Logan, Utah) respectively. Medium and supplements were combined according to manufacturer's instructions.

Clonal Embryonic Progenitor Line Nomenclature:

The cell lines of the present invention along with their alternative designations are listed in Table 4 along with synonyms that represent minor modifications that result from the manipulation of the names resulting from bioinformatics analysis, including the substitution of "−" for "." and vice versa, the inclusion of an "x" before cell line names beginning with an arabic number, and suffixes such as "bio1" or "bio2" that indicate biological replicates of the same line which are examples of cases where a frozen ampule of the same line was thawed, propagated, and used in a parallel analysis and "Rep1" or "Rep2" which indicate technical replicates wherein RNA isolated from a given cell line is utilized a second time for a repeat analysis without thawing or otherwise beginning with a new culture of cells. Passage number (which is the number of times the cells have been trypsinized and replated) for the cell lines is usually designated by the letter "P" followed by an arabic number, and in contrast, the population doubling number (which refers to the number of estimated doublings the cell lines have undergone in clonal expansion from one cell) is designated by the letters "PD" followed by an arabic number. The number of PDs in a passage varied from experiment to experiment but generally each trypsinization and replating was at a 1:3 to 1:4 ratio (corresponding to an increase of PDs of 1.5 and 2 respectively). In the expansion of clones, the original colonies were removed from tissue culture plates with cloning cylinders, and transferred to 24-well plates, then 12-well, and 6-well as described above. First confluent 24 well is designated P1, the first confluent 12 well culture is P2, the first 6-well culture is P3, then the six well culture was then split into a second 6 well plate (P4) and a T25 (P4). The second 6 well at P4 is utilized for RNA extraction (see U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety) and represents about 18-21 PD of clonal expansion. Typical estimated subsequent passages and PDs are the following split to a T75 flask (19.5-22.5 PD), the P6 passage of the cells to a T225 flask (21-24 PD), then P7 being the transfer of the cells to a roller bottle (850 cm², 23-26 PD), and P8 the split into 4 rollers (25-28 PD). The ranges shown above in parenthesis represent estimated ranges in cell counts due to cell sizes, attachment efficiency, and counting error.

Propagation of Clonal, Pooled Clonal, Oligoclonal, and Pooled Oligoclonal Cell Lines.

Aspects of the invention provide methods for identifying and differentiating embryonic progenitor cell lines that are derived from a single cell (clonal) or cell lines that are "pooled clonal" meaning that cell lines cloned have indistinguishable markers such as gene expression markers and are combined to produce a single cell culture often for the purpose of increasing the number of cells in a culture, or are oligoclonal wherein a line is produced from a small number, typically 2-1,000 similar cells and expanded as a cell line, or "pooled oligoclonal" lines which are lines produced by combining two or more oligoclonal cell lines that have indistinguishable markers such as patterns of gene expression. Said clonal, pooled clonal, oligoclonal, or pooled oligoclonal cell lines are then propagated in vitro through removal of the cells from the substrate to which they are affixed, and the re-plating of the cells at a reduced density of typically ⅓ to ¼ of the original number of cells, to facilitate further proliferation. Examples of said cell lines and their associated cell culture media is disclosed in U.S. patent application Ser. No. 12/504,630 filed on Jul. 16, 2009 and titled "Methods to Accelerate the Isolation of Novel Cell Strains from Pluripotent Stem Cells and Cells Obtained Thereby"; and West et al., 2008, Regenerative Medicine vol. 3(3) pp. 287-308, both of which are incorporated herein by reference, including supplemental information. The compositions and methods of the present invention relate to said cell lines cultured as described but for greater than 21 doublings of clonal expansion.

Gene Expression Analysis

To reduce variations in gene expression due to cell cycle artifacts, and to capture an early gene expression profile of the cells, upon being expanded to six well plates, on the day the cells reached confluence, the cells were placed in media with a reduction of serum to 0.5% in the case where the original serum concentration was >5%. In all other cases, serum and/or other growth factors was reduced to 10% of their original values. These quiescence conditions were imposed for five days and all cultures were re-fed two days prior to harvest to reduce feeding difference artifacts. So, by way of example, if the original media was DMEM medium with 10% FCS, then the quiescence synchronization media was DMEM with 0.5% FCS. Total RNA was extracted directly from cells growing in 6-well or 6 cm tissue culture plates using Qiagen RNeasy mini kits according to the manufacturer's instructions. RNA concentrations were measured using a Beckman DU530 or Nanodrop spectrophotometer and RNA quality determined by denaturing agarose gel electrophoresis or an Agilent 2100 bioanalyzer. Whole-genome expression analysis was carried out using Affymetrix Human Genome U133 Plus 2.0 GeneChip® system, Illumina Human-6 v1 and HumanRef-8 v1 Beadchips (Illumina 1), and Illumina Human-6 v2 Beadchips (Illumina 2), and RNA levels for certain genes were confirmed by quantitative PCR. For Illumina BeadArrays, total RNA was linearly amplified and biotin-labeled using Illumina TotalPrep kits (Ambion), and cRNA was quality controlled using an Agilent 2100 Bioanalyzer. cRNA was hybridized to Illumina BeadChips, processed, and read using a BeadStation array reader according to the manufacturer's instructions (Illumina). Relative Fluorescence Unit (RFU) values for all of the cell lines with common probe sets were quantile normalized.

Data from the gene expression analysis above can be found in the Supplementary Tables from West et al., 2008, Regenerative Medicine vol. 3(3) pp. 287-308, incorporated by reference herein in its entirety, including all Supplementary Tables. In Supplementary Tables II-IV, the genes are displayed in rank order (highest-lowest) for the ratio of (highest RFU value observed for the gene in the entire set of cell lines—Average RFU value)/Ave RFU value. In Supplementary Table V, the top 45 differentially expressed genes are rank ordered (highest-lowest) for the ratio of (highest RFU value observed for the gene in the individual cell line)/Ave RFU value for all cell lines. In Supplementary Table VI, the genes corresponding to recognized CD antigens are displayed in rank order (highest-lowest) and also (lowest to highest) for the ratio of (highest RFU value observed for the gene in the entire set of cell lines)/Ave RFU value and (lowest RFU value observed for the gene in the entire set of cell lines)/Ave RFU value, respectively. In Supplementary Table VII, the genes corresponding to secreted proteins are displayed in rank order (highest-lowest) for the ratio of (highest RFU value observed for the gene in the entire set of cell lines)/Ave RFU value.

Exemplary Conditions for Inducing Chondrocyte Differentiation

It is noted that any convenient method for inducing chondrogenesis (or cartilage production) using the progenitor cell lines described herein may be employed (either in vivo or in vitro) for either research or therapeutic purposes, and as such, no limitation in this regard is intended. The assays described below thus represent exemplary, non-limiting examples of conditions for chondrogenesis.

Micromass Differentiation Protocol 1

The following differentiation protocol is simply referred to as "d14 MM" (e.g., in the microarray tables described herein).

1. Cells are cultured in gelatin (0.1%) coated Corning tissue culture treated cultureware and detached with 0.25% trypsin/EDTA (Gibco) diluted 1:3 with PBS (Gibco Ca, Mg free). After detachment and addition of growth medium cells are counted using a Coulter counter and appropriate number of cells needed for experiment (e.g. 10×10e6 cells or more) are resuspended at a cell density of 20×10e6 cells/ml in growth medium.

2. 10 ul aliquots are seeded as mounds or "micromasses" onto Corning Tissue Culture Treated Polystyrene plates or dishes. Twenty five or more micromass aliqouts (200,000 cells/10 ul aliquot) are seeded.

3. The seeded micromasses are placed in a humidified incubator at 37° with 5% O2 and 10% CO2 for 90 minutes to 2 hours for attachment.

4. Growth medium is added and the following morning is replaced, after aspiration and washing with PBS (Ca, Mg free), with Complete Chondrogenic Medium (prepared as described below for the pellet micromasses). For example 6 ml Complete Chondrogenic medium/10 cm dish is added. Cells are maintained in a humidified incubator at 37° with 5% $O_2$, 10% $CO_2$ and chondrogenic medium replaced with freshly prepared medium every 2-3 days.

5. After varying periods of time in chondrogenic medium RNA is extracted using Qiagen RNeasy kits (Qiagen Cat. No. 74104) as described in the Qiagen Handbook. RNA yield is maximized by using Qiagen's QiaShredder (Cat. #79654 to homogenize samples following lysis of micromasses with RLT buffer, (which is provided with the RNeasy mini kits) prior to RNA extraction.

An alternative to Lonza Chondrogenic medium is CellGro (Cat. No. 15-013-CV) from Media Tech. To each 500 ml, the following supplements are added: 5.0 ml Pen/Strep (Gibco Cat. No. 15140), 5.0 ml Glutamax (Gibco Cat. No. 35050), Dexamethasone (Sigma, St. Louis, Mo., Cat. No. D1756-100)-500 ul of 0.1 mM for a final concentration of 0.1 uM; L-Proline (Sigma Cat. No. D49752)—500 ul 0.35M for a final concentration of 0.35 mM; Ascorbic Acid-2-phosphate (Sigma, Cat. No. 49792, Fluka)—500 ul 0.17M for a final concentration 0.17 mM; ITS Premix (BD, Franklin Lakes, N.J., sterile Cat. No. 47743-628)—500 ul of 1000× concentrate for a final concentration of 6.25 ug/ml insulin, 6.25 ug/ml transferrin, 6.25 ng/ml selenious acid, serum albumin 1.25 mg/ml, 5.35 ug/ml linoleic acid.

Following addition of constituents above the media is filtered through a 500 ml Corning 0.2 micron filter unit.

Micromass Differentiation Protocol 2

The following differentiation protocol is simply referred to as "d14 MM" in the microarray tables described herein.

As an alternative to Lonza TGFβ3 described above we use TGFβ3 (R&D Systems, Minneapolis Minn., Cat. No. 243-B3-010). It is prepared, aliquoted and stored and used similarly to that purchased from Lonza.

Micromass Differentiation Protocol 3

The following differentiation protocol is simply referred to as "d14 CS" in the microarray tables described herein.

As an alternative to Micromass Protocol 1, cells may be plated in the Complete Chondrogenic medium directly rather than allowing the micromasses to attach in the presence of serum-containing medium. Said differentiated micromasses are designated "Chondro-seeded", or "CS" in the present invention.

Pellet Differentiation Protocol

The following differentiation protocol is simply referred to as "d14 Pel" in the microarray tables described herein.

1. Cells are cultured in gelatin (0.1%) coated Corning tissue culture treated cultureware and detached with 0.25% trypsin/EDTA (Invitrogen, Carlsbad, Calif., Gibco) diluted 1:3 with PBS (Ca, Mg free). After detachment and addition of growth medium cells are counted using a Coulter counter and appropriate number of cells needed for experiment (e.g. 10×10e6 or more) are transferred into a sterile polyproylene tube and spun at 150 g for 5 min at room temperature.

2. The supernatant is aspirated and discarded. The cells are washed with the addition of Incomplete Chondrogenic Medium consisting of hMSC Chondro BulletKit (PT-3925) to which is added supplements (Lonza, Basel, Switzerland, Poietics Single-Quots, Cat. #PT-4121). Supplements added to prepare Incomplete Chondrogenic Medium are: Dexamethasone (PT-4130G), Ascorbate (PT-4131G), ITS+supplements (4113G), Pyruvate (4114G), Proline (4115G), Gentamicin (4505G), Glutamine (PT-4140G).

3. Cells are spun at 150 g at room temperature, the supernatant is aspirated and cell the pellet is resuspended (once more) with 1.0 ml Incomplete Chondrogenic Medium per 7.5×105 cells, and spun at 150×g for 5 minutes. The supernatant is aspirated and discarded. The Chondrogenesis culture protocol as described by Lonza is followed with some modifications (as written below).

4. Cell pellets are resuspended in Complete Chondrogenic medium to a concentration of 5.0×105 cells per ml. Complete Chondrogenic Medium consists of Lonza Incomplete Medium plus TGFb3 (Lonza, PT-4124). Sterile lyophilized TGFb3 is reconstituted with the addition of sterile 4 mM HCl containing 1 mg/ml BSA to a concentration of 20 ug/ml and is stored after aliquoting at −80° C. Complete Chondrogenic medium is prepared just before use by the addition of 1 ul of TGFb3 for each 2 ml of Incomplete Chondrogenic medium (final TGFb3 concentration is 10 ng/ml).

5. An aliquot of 0.5 ml ($2.5 \times 10^5$ cells) of the cell suspension is placed into sterile 15 ml polypropylene culture tubes. Cells are spun at 150×g for 5 minutes at room temperature.

6. Following centrifugation the caps of the tubes are loosened one half turn to allow gas exchange. The tubes are placed in an incubator at 37° C., in a humidified atmosphere of 10% $CO_2$ and 5% $O_2$. Pellets are not disturbed for 24 hours.

7. Cell pellets are fed every 2-3 days by completely replacing the medium in each tube by aspirating the old medium with sterile 1-200 ul pipette tip and adding 0.5 ml of freshly prepared Complete Chondrogenic Medium to each tube.

8. After replacing the medium and ensuring that the pellet is free-floating, caps are loosened and tubes returned to the incubator.

9. Pellets are harvested after varying time points in chondrogenic medium and prepared for histology by fixation with Neutral Buffered Formalin and/or the pellets are combined and prepared for RNA extraction using RNeasy mini Kits (Qiagen, Germantown, Md., Cat. No. 74104).

The protocol for RNA extraction is followed as described by the Qiagen Handbook. RNA yield is maximized by using Qiagen's QiaShredder (Cat. #79654) to homogenize samples following lysis of cell pellets with RLT buffer (provided in RNeasy mini kits) prior to RNA extraction.

Alginate Bead Differentiation Protocol

The following differentiation protocol is simply referred to as "d14 alginate" in the microarray tables described herein.

Cells of the present invention are pelleted by centrifugation at low speed, washed with NaCl (155 mM) centrifuged again, and the pellet was resuspended at $20 \times 10^6$ in 1.2% alginate (Lonza). The cell suspension was drawn into a 1 ml syringe and through a 22 g needle was dispensed dropwise into a $CaCl_2$ bath (102 mM). Gelation is immediate. Beads were washed 3-5× with NaCl (155 mM), then washed once with Chondrogenic medium (without TGF) following immersion in chondrogenic medium. The beads were placed in multiple wells of 6 well plates and fed three days a week for 14 days. Beads were then washed with NaCl multiple times before depolymerization by exposure to sodium citrate (55 mM) for 20 minutes. After spinning, the cell pellet was lysed with RLT (Qiagen) and total RNA extracted using RNeasy micro kits (Qiagen) following a shredding step using QiaShredder to improve yield. COL2A1 expression was determined by qPCR as above.

Gene Expression Markers of Chondrocyte Differentiation

Chondrocyte gene expression may be assayed by microarray analysis as described herein or by qPCR. qPCR rimer sequences may be chosen by means known in the art and by way of nonlimiting example may be:

| COMP | f2 | CCGACAGCAACGTGGTCTT |
|------|----|---------------------|
| COMP | r2 | CAGGTTGGCCCAGATGATG |
| CRTL1 | f1 | TGCTCAGATTGCAAAAGTGG |
| CRTL1 | r1 | TATCTGGGAAACCCACGAAG |
| CILP | f1 | CCTGGTCCTGGAAGTCACAT |
| CILP | r1 | CCATGTTGTCCACTCACCAG |
| CEP68 | f1 | ATCCGTAGAGAGCACGGAGA |
| CEP68 | r1 | GGACTCTCCATGGGACAAGA |

-continued

| Gene | Primer | Sequence |
|---|---|---|
| COL2A1 | f3 | GGCAATAGCAGGTTCACGTACA |
| COL2A1 | r3 | CGATAACAGTCTTGCCCCACTT |
| COL2A1 | f4 | TGGCCTGAGACAGCATGA |
| COL2A1 | r4 | AGTGTTGGGAGCCAGATTG |
| CEP68 | f1 | ATCCGTAGAGAGCACGGAGA |
| CEP68 | r1 | GGACTCTCCATGGGACAAGA |
| SOX9 | f1 | TACGACTACACCGACCACCA |
| SOX9 | r1 | TCAAGGTCGAGTGAGCTGTG |
| SCXA | f1 | TCCAGCTACATCTCGCACCT |
| SCXA | r1 | CGGTCCTTGCTCAACTTTCT |
| BARX2 | f1 | GGACTTGGCTCAGTCTCTGG |
| BARX2 | r1 | TGGGGATGGAGTTCTTCTTG |
| GAPDH | f2 | GGCCTCCAAGGAGTAAGACC |
| GAPDH | r2 | AGGGGTCTACATGGCAACTG |
| RPS10 | f1 | ATTTGGTCGTGGACGTGGT |
| RPS10 | r1 | TTTGGCTGTAAGTTTATTCAATGC |
| GUSB | f1 | AAACGATTGCAGGGTTTCAC |
| GUSB | r1 | CTCTCGTCGGTGACTGTTCA |

Other Primers Sets for Chondrogenesis:

| Gene | Primer | Sequence |
|---|---|---|
| COL2A1 | f1 | TCTACCCCAATCCAGCAAAC |
| COL2A1 | r1 | GTTGGGAGCCAGATTGTCAT |
| COL2A1 | f2 | CACACTGGTAAGTGGGGCAAGACCG |
| COL2A1 | r2 | ACGAGGTCCTCACTGGTGAA |
| ACAN | f1 | TGAGTCCTCAAGCCTCCTGT |
| ACAN | r1 | TGGTCTGCAGCAGTTGATTC |
| ACAN | f2 | ACAGCTGGGGACATTAGTGG |
| ACAN | r2 | GTGGAATGCAGAGGTGGTTT |
| COL10A1 | f1 | GCTAAGGGTGAAAGGGGTTC |
| COL10A1 | r1 | CTCCAGGATCACCTTTTGGA |
| BGN | f1 | GGACTCTGTCACACCCACCT |
| BGN | r1 | AGCTCGGAGATGTCGTTGTT |
| COL9A2 | f1 | AGCATCATTCGGCTGTTACC |
| COL9A2 | r1 | CTGAGGGGTGGAACTGTAGC |
| CDMP1 | f1 | CCCATCAGCATCCTCTTCAT |
| CDMP1 | r1 | TGTAGATGCTCCTGCCACAG |
| VERSICAN | f1 | ACCACGCTTCCTATGTGACC |
| VERSICAN | r1 | TGTTGTAACTGGGTGGCAAA |
| COL11A1 | f1 | TCGAGGGTTTGATGGACTTC |
| COL11A1 | r1 | CATCTTCTCCCCTCATTCCA |
| DCN | f1 | TGGCAACAAAATCAGCAGAG |
| DCN | r1 | GCCATTGTCAACAGCAGAGA |
| FMOD | f1 | CCTCCAAGGCAATAGGATCA |
| FMOD | r1 | GCTGCGCTTGATCTCGTTC |
| LUM | f1 | TGATCTGCAGTGGCTCATTC |
| LUM | r1 | AAAAGAGCCCAGCTTTGTGA |
| COL1A1 | f1 | GTGCTAAAGGTGCCAATGGT |
| COL1A1 | r1 | ACCAGGTTCACCGCTGTTAC |
| COL1A1 | f2 | GTGCTAAAGGTGCCAATGGT |
| COL1A1 | r2 | CTCCTCGCTTTCCTTCCTCT |
| PRELP | f1 | TCCCAATCTTGCCTTCATTC |
| PRELP | r1 | GTCATGGAACGCCACTAGGT |
| ACAN | f3 | TCGAGGACAGCGAGGCC |
| ACAN | r3 | TCGAGGGTGTAGCGTGTAGAGA |
| COL10A1 | f2 | CAAGGCACCATCTCCAGGAA |
| COL10A1 | r2 | AAAGGGTATTTGTGGCAGCATATT |
| CRTL1 | f2 | TTCCACAAGCACAAACTTTACACAT |
| CRTL1 | r2 | GTGAAACTGAGTTTTGTATAACCTCTCAGT |
| LUM | f2 | ACCAGATTGACCATATTGATGA |
| LUM | r2 | GGACAGATCCAGCTCAACC |
| SOX9 | f2 | AGGCAAGCAAAGGAGATGAA |
| SOX9 | r2 | TGGTGTTCTGAGAGGCACAG |
| SOX9 | f3 | ACTGAGTCATTTGCAGTGTTTCTGCC |
| SOX9 | r3 | GTGGGCTGATCCCCTCCAGGT |
| SOX5 | f1 | TGGCACTGCACTGGGTAGGA |
| SOX5 | r1 | AAGGCTGGGAGCCCGTCACT |
| AGC1/ACAN | f4 | TGAGTCCTCAAGCCTCCTGT |
| AGC1/ACAN | r4 | CCTCTGTCTCCTTGCAGGTC |
| IHH | f1 | GGCCGGGAGACCGTGTTG |
| IHH | r1 | TGGGGCTCGCGGTCCAGTAA |
| IHH | f2 | TACGCCTGGAGAGTGGGGCG |
| IHH | r2 | TGGGGCTCGCGGTCCAGTAA |
| COL2A1 | f5 | TCGTGGGTCCCAGGGGTGAA |
| COL2A1 | r5 | GACCTGGAGGGCCCTGTGCG |
| COL2A1 | f6 | TGCTGCCCCATCTGCCCAAC |
| COL2A1 | r6 | CCTGCAGGTCCCTGAGGCCC |
| COL2A1 | f7 | AGGGCCAGGATGTCCGGCAA |
| COL2A1 | r7 | TCTGCCACGAGGTCCAGGGG |
| CRTAC1 (CEP-68) | f2 | CGGGGCGATGGCACCTTTGT |
| CRTAC1 (CEP-68) | r2 | GATAGAGGCGGTGGGGGCCA |
| COMP | f1 | ACAATGACGGAGTCCCTGAC |

-continued

| | | |
|---|---|---|
| COMP | r1 | TCTGCATCAAAGTCGTCCTG |
| BARX2 | f2 | GAGTCAGAGACGGAACAGCC |
| BARX2 | r2 | AGTCCCAGAGACTGAGCCAA |
| CHM1 (LECT1) | f1 | GCGCAAGTGAAGGCTCGTAT |
| CHM1 (LECT1) | r1 | GTTTGGAGGAGATGCTCTGTTTG | qPCR, protocols may vary and are well-known in the art. By way of nonlimiting example, samples for testing are prepared in standard Optical 96-well reaction plates (Applied Biosystems Carlsbad, Calif., PN 4306737) consisting of 30 ng of RNA equivalent of cDNA, 0.4 uM per primer, Ultra-Pure distilled water (Invitrogen), diluted 1:1 with 12.5 ul of Power SYBR Green PCR Master Mix (Applied Biosystems Carlsbad, Calif., Cat#4367659) incorporating AmpliTaq Gold DNA polymerase in a total reaction volume of 25 ul. Real-Time qPCR is run using Applied Biosystems 7500 Real-Time PCR System employing SDSv1.2 software. Amplification conditions are set at 50° C. for 2 min. (stage 1), 95° C. for 10 min. (stage 2), 40 cycles of 95° C. for 15 sec then 60° C. for 1 min (stage 3), with a dissociation stage at 95° C. for 15 sec, 60° C. for 1 min, and 95° C. for 15 sec (stage 4). Ct values for amplification products of genes of interest are normalized to the average Ct value of 3 housekeeping genes (GAPD, RPS10, and GUSB).

Safranin O Staining Assay

The well-known techniques of staining of formalin-fixed, paraffin-embedded tissue sections with Safranin O are commonly used in the detection of cartilage-related proteoglycans, however, the assay is not absolutely specific to cartilage since it also stains mucin, mast cell granules, and likely other substances in other cell types. A nonlimiting example of the protocol where cartilage and mucin will be stained orange to red, and the nuclei will be stained black and the background stained green uses formalin-fixed micromasses, pellets, or similar aggregations of cells. Reagents used include Weigert's Iron Hematoxylin Solution: in which Stock Solution A composed of 1 gram of Hematoxylin in 100 ml of 95% Alcohol; Stock Solution B composed of 4 ml of 29% Ferric chloride in water diluted in 95 ml of Distilled water and 1.0 ml of concentrated Hydrochloric acid; Weigert's Iron Hematoxylin Working Solution composed of equal parts of stock solution A and B and used within four weeks; 0.001% Fast Green (FCF) Solution composed of 0.01 gram of Fast green, FCF, C.I. 42053 in 1000 ml Distilled water; 1% Acetic Acid Solution composed of 1.0 ml glacial acetic acid in 99 ml Distilled water; and 0.1% Safranin O Solution composed of 0.1 gram Safranin O, C.I. 50240 in 100 ml Distilled water. Samples are Deparaffinized and hydrated with distilled water. They are stained with Weigert's iron hematoxylin working solution for 10 minutes, then washed in running tap water for 10 minutes, stained with fast green (FCF) solution for 5 minutes, rinsed quickly with 1% acetic acid solution for no more than 10-15 seconds, stained in 0.1% safranin O solution for 5 minutes, dehydrated and cleared with 95% ethyl alcohol, absolute ethyl alcohol, and xylene, using 2 changes each, 2 minutes each, mounted using resinous medium, and imaged and analyzed for stains as described above. Cartilage-related proteoglycan stains dark red-orange.

Low Throughput Screening and qPCR

The clonal, oligoclonal, or pooled clonal or pooled oligoclonal embryonic progenitor cell lines of the present invention at either <21 or preferably >21 doublings of clonal or oligoclonal expansion, most preferably at 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 doublings of clonal expansion (since before 29 doublings of clonal expansion the cells are available only in limited quantities, and beyond 70 doublings the cells normally approach senescence) are screened simultaneously in 1, 2, 3, 4, 5, or preferably 10 or more diverse differentiation conditions. The differentiation conditions may include those described above as "micromass differentiation," "pellet differentiation," and "alginate bead differentiation."

The readout of the assay can be mRNA markers of chondrocyte differentiation including but not limited to those described above as "Gene Expression Markers of Chondrocyte Differentiation" and measured by hybridization to arrayed target sequences, including but not limited to microarrays or by qPCR. Detection can also be at the level of peptides or proteins that may be detected through the use of specific antibodies, through the use of enzyme assays, mass spectroscopy, or other similar means well known in the art.

Medium Throughput Screen of the Fate Space of Clonal or Oligoclonal Embryonic Progenitors.

The clonal, oligoclonal, or pooled clonal or pooled oligoclonal embryonic progenitor cell lines of the present invention at either <21 or preferably >21 doublings of clonal or oligoclonal expansion, most preferably at 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 doublings of clonal expansion (since before 29 doublings of clonal expansion the cells are available only in limited quantities, and beyond 70 doublings the cells normally approach senescence) are screened simultaneously in 10, 20, 30, 40, 50, or preferably 100 or more diverse differentiation conditions (see, e.g., differentiation conditions described in U.S. patent application Ser. No. 11/604,047 filed on Nov. 21, 2006 and titled "Methods to Accelerate the Isolation of Novel Cell Strains from Pluripotent Stem Cells and Cells Obtained Thereby"; and U.S. patent application Ser. No. 12/504,630 filed on Jul. 16, 2009 and titled "Methods to Accelerate the Isolation of Novel Cell Strains from Pluripotent Stem Cells and Cells Obtained Thereby", each incorporated herein by reference). The cells are cultured in said differentiation conditions for 1-6 weeks, most preferably four weeks.

The readout of the assay can be mRNA markers of differentiation such as those described above as "Gene Expression Markers of Chondrocyte Differentiation" and measured by hybridization to arrayed target sequences, including but not limited to microarrays or PCR. Detection can also be at the level of peptides or proteins that may be detected through the use of specific antibodies, through the use of enzyme assays, mass spectroscopy, or other similar means well known in the art.

Medium Throughput qPCR Screen of hEP Cell Differentiation

The clonal, oligoclonal, or pooled clonal or pooled oligoclonal embryonic progenitor cell lines of the present invention including but not limited to those described above at either <21 or preferably >21 doublings of clonal or oligoclonal expansion, most preferably at 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 doublings of clonal expansion are plated in 12 well culture plates with each well having 10 micromasses of 250, 000 cells (i.e. 2.5 million cells per well). Alternatively the cells are treated with other culture conditions (e.g., as described in U.S. patent application Ser. No. 11/604,047 filed on Nov. 21, 2006 and titled "Methods to Accelerate the Isolation of Novel Cell Strains from Pluripotent Stem Cells and Cells Obtained Thereby"; and U.S. patent application Ser. No. 12/504,630 filed on Jul. 16, 2009 and titled "Methods to Accelerate the Isolation of Novel Cell Strains from Pluripotent Stem Cells and Cells Obtained Thereby", each incorporated herein by reference; see Table II using the same number of cells, exposed to any combination of the culture media listed in Table III, and supplemented factors listed in Table IV of these applications). The cells are cultured in said differentiation conditions for 1-6 weeks, most preferably four weeks.

RNA is prepared from cell lysates using the RNeasy mini kits (Qiagen) according to the manufacturer's instructions. Briefly, cell cultures (micromasses) are rinsed in PBS, then lysed in a minimal volume of the RLN lysis buffer. After incubation on ice, the cell debris is removed by centrifugation and the lysate is mixed with RLT buffer, after which ethanol is added to the mixture. The combined mixture is then loaded onto the RNeasy spin column and centrifuged. The loaded column is then washed and the purified RNA is released from the column with a minimal volume of DEPC-treated water (typically 30 ul or less). The concentration of RNA in the final eluate is determined by absorbance at 260 nm.

cDNA synthesis is performed using the SuperScript First Strand cDNA kit (InVitrogen; Carlsbad, Calif.). Briefly, 2.5 ug of purified RNA is heat denatured in the presence of random hexamers. After cooling, the first strand reaction is completed using SuperSript reverse transcriptase enzyme and associated reagents from the kit. The resulting product is further purified using QIAquick PCR Purification kits (Qiagen) according to the manufacturer's instructions. Briefly, PB buffer is added to the first strand cDNA reaction products, then the mixture is loaded onto the QIAquick spin column and centrifuged. The column is washed with PE buffer and the purified cDNA is eluted from the column using a minimal volume of water (20 ul).

qPCR primer pairs are synthesized for each target gene. Briefly, primer pairs for a target gene are designed to amplify only the target mRNA sequence and optimally have annealing temperatures for their target sequences that lie in the range of 65-80° C. and unique amplification products in the size range of 100-500 bp. Primer pairs are supplied at working concentrations (10 uM) to BioTrove, Inc. (Woburn, Mass.) for production of a custom qPCR Open Array plate. OpenArray plates are designed to accommodate 56-336 primer pairs and the final manufactured plate with dried down primer pairs is provided to the service provider. Purified cDNA reaction products (2.) and Syber green master mix are loaded into individual wells of the OpenArray plate using OpenArray autoloader device (BioTrove). The plate is sealed and the qPCR and loaded into the NT Imager/Cycler device (BioTrove) for amplification. Ct values for each sample are calculated using the OpenArray application software.

Applications

The disclosed methods for the culture of animal cells and tissues are useful in generating cells or progeny thereof in mammalian and human cell therapy, such as, but not limited to, generating human cells and cell-derived formulations useful in treating orthopedic conditions including but not limited to arthritis such as osteoarthritis, degeneration of intervertebral tissue, temporal mandibular joint disease, trauma or surgical repair of cartilaginous tissues of the nose, outer ear, mandibular joint, trachea, crichoid, sternum, or other synovial joints such as those of the shoulder, elbow, wrist, fingers and weight-bearing joint such as the hip, knee, ankle, and toes.

In certain embodiments of the invention, single cell-derived and oligoclonal cell-derived cells derived by methods of this invention, are utilized in research and treatment of disorders relating to cell biology, cell-based drug discovery and in cell therapy. The single cell-derived cell populations derived using the methods of the present invention may already have received the requisite signals to be directed down a differentiation pathway.

In certain embodiments of the invention, single cell-derived and oligoclonal cell-derived cells are introduced into the tissues in which they normally reside in order to exhibit therapeutic utility. In certain embodiments of the invention, single cell-derived and oligoclonal cell-derived cells, derived by methods of this invention, are utilized in inducing the differentiation of other pluripotent stem cells. The generation of single cell-derived populations of cells capable of being propagated in vitro while maintaining an embryonic pattern of gene expression is useful in inducing the differentiation of other pluripotent stem cells. Cell-cell induction is a common means of directing differentiation in the early embryo. Many potentially medically-useful cell types are influenced by inductive signals during normal embryonic development, including spinal cord neurons, cardiac cells, pancreatic beta cells, and definitive hematopoietic cells. Single cell-derived populations of cells capable of being propagated in vitro while maintaining an embryonic pattern of gene expression can be cultured in a variety of in vitro, in ovo, or in vivo culture conditions to induce the differentiation of other pluripotent stem cells to become desired cell or tissue types. Induction may be carried out in a variety of methods that juxtapose the inducer cell with the target cell. By way of nonlimiting examples, the inducer cells may be plated in tissue culture and treated with mitomycin C or radiation to prevent the cells from replicating further. The target cells are then plated on top of the mitotically-inactivated inducer cells. Alternatively, single cell-derived inducer cells may be cultured on a removable membrane from a larger culture of cells or from an original single cell-derived colony and the target cells may be plated on top of the inducer cells or a separate membrane covered with target cells may be juxtaposed so as to sandwich the two cell layers in direct contact. The resulting bilayer of cells may be cultured in vitro, transplanted into a SPF avian egg, or cultured in conditions to allow growth in three dimensions while being provided vascular support (see, for example, international patent publication number WO2005068610, published Jul. 28, 2005, the disclosure of which is hereby incorporated by reference). The inducer cells may also be from a source of pluripotent stem cells, including hES or hED cells, in which a suicide construct has been introduced such that the inducer cells can be removed at will. Cell types useful in single cell-derived and oligoclonal cell-derived induction may include cases of induction well known in the art to occur naturally in normal embryonic development. In certain embodiments of the invention, single cell-derived cells and oligoclonal cell-derived cells, derived by methods of this invention, are used as "feeder cells" to support the growth of other cell types, including pluripotent stem cells. The use of single cell-derived cells and oligoclonal cell-derived cells of the present invention as feeder cells alleviates the potential risk of transmitting pathogens from feeder cells derived from other mammalian sources to the target cells. The feeder cells may be inactivated, for example, by gamma ray irradiation or by treatment with mitomycin C, to limit replication and then co-cultured with the pluripotent stem cells.

In certain embodiments of the invention, the extracellular matrix (ECM) of single cell-derived and oligoclonal cell-derived cells, derived by methods of this invention, may be used to support less differentiated cells (see Stojkovic et al., Stem Cells (2005) 23(3):306-14). Certain cell types that normally require a feeder layer can be supported in feeder-free culture on a matrix (Rosler et al., Dev Dyn. (2004) 229(2): 259-74). The matrix can be deposited by preculturing and lysing a matrix-forming cell line (see WO 99/20741), such as the STO mouse fibroblast line (ATCC Accession No. CRL-1503), or human placental fibroblasts.

In certain embodiments of the invention, the conditioned media of single cell-derived and oligoclonal cell-derived cell cultures may be collected, pooled, filtered and stored as conditioned medium. This conditioned medium may be formulated and used for research and therapy. Such conditioned medium may contribute to maintaining a less differentiated state and allow propagation of cells such as pluripotent stem cells. In certain embodiments of the invention, conditioned medium of single cell-derived and oligoclonal cell-derived cell cultures derived by the methods of this invention can be used to induce differentiation of other cell types, including pluripotent stem cells. The use of conditioned medium of single cell-derived and oligoclonal cell-derived cell cultures may be advantageous in reducing the potential risk of exposing cultured cells to non-human animal pathogens derived from other mammalian sources (i.e. xenogeneic free).

In another embodiment of the invention, cell types that do not proliferate well under any known cell culture conditions may be induced to proliferate such that they can be isolated clonally or oligoclonally according to the methods of this invention through the regulated expression of factors that overcome inhibition of the cell cycle, such as regulated expression of SV40 virus large T-antigen (Tag), or regulated E1a and/or E1b, or papillomavirus E6 and/or E7, or CDK4 (see, e.g., U.S. patent application Ser. No. 11/604,047 filed on Nov. 21, 2006 and titled "Methods to Accelerate the Isolation of Novel Cell Strains from Pluripotent Stem Cells and Cells Obtained Thereby", incorporated herein by reference).

In another embodiment of the invention, the factors that override cell cycle arrest may be fused with additional proteins or protein domains and delivered to the cells. For example, factors that override cell cycle arrest may be joined to a protein transduction domain (PTD). Protein transduction domains, covalently or non-covalently linked to factors that override cell cycle arrest, allow the translocation of said factors across the cell membranes so the protein may ultimately reach the nuclear compartments of the cells. PTDs that may be fused with factors that override cell cycle arrest include the PTD of the HIV transactivating protein (TAT) (Tat 47-57) (Schwarze and Dowdy 2000 *Trends Pharmacol. Sci.* 21: 45-48; Krosl et al. 2003 *Nature Medicine* (9): 1428-1432). For the HIV TAT protein, the amino acid sequence conferring membrane translocation activity corresponds to residues 47-57 (Ho et al., 2001, *Cancer Research* 61: 473-477; Vives et al., 1997, *J. Biol. Chem.* 272: 16010-16017). These residues alone can confer protein translocation activity.

In another embodiment of the invention, the PTD and the cycle cycle arrest factor may be conjugated via a linker. The exact length and sequence of the linker and its orientation relative to the linked sequences may vary. The linker may comprise, for example, 2, 10, 20, 30, or more amino acids and may be selected based on desired properties such as solubility, length, steric separation, etc. In particular embodiments, the linker may comprise a functional sequence useful for the purification, detection, or modification, for example, of the fusion protein.

In another embodiment of the invention, single cell-derived or oligoclonal cell-derived cells of this invention may be reprogrammed to an undifferentiated state through novel reprogramming technique, as described in U.S. application No. 60/705,625, filed Aug. 3, 2005, U.S. application No. 60/729,173, filed Oct. 20, 2005; U.S. application No. 60/818,813, filed Jul. 5, 2006, the disclosures of which are incorporated herein by reference. Briefly, the cells may reprogrammed to an undifferentiated state using at least a two, preferably three-step process involving a first nuclear remodeling step, a second cellular reconstitution step, and finally, a third step in which the resulting colonies of cells arising from step two are characterized for the extent of reprogramming and for the normality of the karyotype and quality. In certain embodiments, the single cell-derived or oligoclonal cell-derived cells of this invention may be reprogrammed in the first nuclear remodeling step of the reprogramming process by remodeling the nuclear envelope and the chromatin of a differentiated cell to more closely resemble the molecular composition of an undifferentiated or a germ-line cell. In the second cellular reconstitution step of the reprogramming process, the nucleus, containing the remodeled nuclear envelope of step one, is then fused with a cytoplasmic bleb containing requisite mitotic apparatus which is capable, together with the transferred nucleus, of producing a population of undifferentiated stem cells such as ES or ED-like cells capable of proliferation. In the third step of the reprogramming process, colonies of cells arising from one or a number of cells resulting from step two are characterized for the extent of reprogramming and for the normality of the karyotype and colonies of a high quality are selected. While this third step is not required to successfully reprogram cells and is not necessary in some applications, the inclusion of the third quality control step is preferred when reprogrammed cells are used in certain applications such as human transplantation. Finally, colonies of reprogrammed cells that have a normal karyotype but not sufficient degree of programming may be recycled by repeating steps one and two or steps one through three.

In another embodiment of the invention, the single cell-derived and oligoclonal cell-derived cells may be used to generate ligands using phage display technology (see U.S. application No. 60/685,758, filed May 27, 2005, and PCT US2006/020552, filed May 26, 2006, the disclosures of which are hereby incorporated by reference).

Measurement of the gene expression levels may be performed by any known methods in the art, including but not limited to, microarray gene expression analysis, bead array gene expression analysis and Northern analysis. The gene expression levels may be represented as relative expression normalized to the ADPRT (Accession number NM_001618.2), GAPD (Accession number NM_002046.2), or other housekeeping genes known in the art. The gene expression data may also be normalized by a median of medians method. In this method, each array gives a different total intensity. Using the median value is a robust way of comparing cell lines (arrays) in an experiment. As an example, the median was found for each cell line and then the median of those medians became the value for normalization. The signal from the each cell line was made relative to each of the other cell lines.

In another embodiment of the invention, the single cell-derived or oligoclonal cell-derived cells of this invention may express unique patterns of CD antigen gene expression, which are cell surface antigens. The differential expression of CD antigens on the cell surface may be useful as a tool, for example, for sorting cells using commerically available antibodies, based upon which CD antigens are expressed by the cells. The expression profiles of CD antigens of some cells of this invention are shown in West et al., 2008, *Regenerative Medicine* vol. 3(3) pp. 287-308, incorporated herein by reference, including supplemental information. For example, there are CD antigens that are expressed in ES cells and not (or in some cases, at reduced levels) in the relatively more differentiated cell lines of this invention. This could be a very useful tool for selecting, sorting, purifying and/or characterizing ES cells. Since the CD antigens are expressed on the cell surface and antibodies to them are, generally speaking, commercially available, antibodies (or specific combinations of them) can be used to purify pure populations of ES cells or cells of this invention out of a heterogeneous mixture of cells. This could be useful in various strategies to grow ES cells or cells of this invention, or prepare these cells for various commercial purposes.

In another embodiment of the invention, the single cell-derived and oligoclonal cell-derived cells, derived by methods of this invention, may be injected into mice to raise antibodies to differentiation antigens. Antibodies to differentiation antigens would be useful for both identifying the cells to document the purity of populations for cell therapies, for research in cell differentiation, as well as for documenting the presence and fate of the cells following transplantation. In general, the techniques for raising antibodies are well known in the art.

A cell produced by the methods of this invention could be genetically modified to produce large amounts of BMP3b or other members of the BMP family, and this cell could therefore be useful in inducing bone in bone-wasting disease. In the case of the cell line of the present invention designated 4D20.8 with markers of mandibular mesenchyme, the overexpression of factors such as BMP3b or other members of the BMP family is useful in the treatment of osteonecrosis or bone fractures, such as that of the mandible.

In another embodiment of the invention, the single cell-derived and oligoclonal cell-derived cells capable of undergoing chondrogenesis may be generated from nonhuman animal species and used in the treatment of veterinary diseases.

In another embodiment of the invention, the single cell-derived and oligoclonal cell-derived cells capable of undergoing chondrogenesis may be used experimentally to perform research on chondrocyte differentiation including the transcriptional regulatory networks that lead to the diverse cartilage types in the human or nonhuman body.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the gene expression patterns of the subject embryonic chondrocyte progenitor cells are specifically embraced by the present invention and are disclosed herein just as if each and every combination was individually and explicitly disclosed. Thus, embryonic chondrocyte progenitor cells that display the markers described are provided herein.

Systems and Kits

Also provided by the subject invention are systems and kits designed for use in various applications as described herein.

For example, systems and kits (referred to generically below as "kits") according to aspects of the invention include one or more of the embryonic chondrocyte progenitor cell lines of the invention. The kits may further include reagents and materials for the propagation and use of the cells for research and/or therapeutic applications as well as instructions for use. The kits may also contain the reagents used herein to induce the differentiation of the cells into chondrocytes, such as the materials described in the protocols above named: Micromass Differentiation Protocol 1, Micromass Differentiation Protocol 2, Micromass Differentiation Protocol 3, Pellet Differentiation Protocol, and Alginate Bead Differentiation Protocol.

In some embodiments, the kit is designed for cartilage production and includes one or more of the embryonic chondrocyte progenitor cell lines described herein and one or more additional components used for the propagation of the cells and/or for including chondrogenesis. The embryonic chondrocyte progenitor cell lines provided in such kits display gene expression markers of the embryonic progenitor lines of the present invention, such as that of the lines: SM30, E15, 4D20.8, 7SMOO32, MEL2, SK11, and 7PEND24. Components for propagation and/or chondrocyte differentiation can include any component described herein for such purposes, including a matrix or a scaffold (or reagents for generating the matrix/scaffolds, e.g., for generating hydrogels), hydrating agents (e.g., physiologically-compatible saline solutions, prepared cell culture media), cell culture substrates (e.g., culture dishes, plates, vials, etc.), cell culture media (whether in liquid or powdered form), antibiotic compounds, hormones, additives, etc.

In certain embodiments, the kit may further include components designed to facilitate the delivery the cell population, e.g., to an experimental animal or to a patient in the need thereof, e.g., a patient in need of cartilage repair/replacement therapy. In these latter embodiments, the components of the kit may be provided in a form that is suitable for therapeutic use (e.g., provided in as sterile/medical grade components). Delivery components can include those designed for encapsulating or immobilizing the cell population (e.g., a scaffold or matrix) as well as for delivering the cells, either directly or in association with other components (e.g., a scaffold or matrix), including injecting the isolated cells into the site of defect, incubating and/or culturing the embryonic progenitor cells with a suitable scaffold or matrix and implanting, incubating with bio-resorbable scaffold, etc. Any convenient scaffolds or matrices, such as bio-resorbable, bio-compatible scaffolds as described in detail above, may be employed, where a number have been employed for, or are being tested for use in, therapeutic cartilage repair/replacement.

In some embodiments, the kit includes components for use in determining that the delivered/transplanted cell population locates to at least one desired site, e.g. site of cartilage damage. Such components may allow the determination of the localization and even quantification of cells delivered cells to a subject.

In certain embodiments, the embryonic chondrocyte progenitor cell line or lines in the kit are genetically modified. For example, an embryonic chondrocyte progenitor cell line may be engineered to express an exogenous gene, e.g., a marker gene that can be used for later identification of cells derived from the cell line (e.g., a reporter gene as is well known in the art). Reporter genes include those that are directly or indirectly detectable, e.g., fluorescent proteins, luminescent proteins, enzymes, cell surface markers, and the like. In certain embodiments, different cell lines re engineered to express exogenous reporter genes that are discriminable from each other, e.g., fluorescent proteins having different excitation and/or emission characteristics.

In certain embodiments, the kit can include any or all components necessary for its intended use.

For example, kits according to the invention may include a number of other suitable articles or components such as artificial joints, tubes, sutures, scalpels, needles, syringes, antiseptics for preparation of surgical sites, orthopedic devices, etc.

Additional types of kits are also provided in aspects of the present invention.

For example, kits are provided for the identification and/or isolation of chondrocyte progenitor cells according to the present invention. Such kits will include reagents designed for detecting the expression of cell markers including any of the gene expression markers described herein. Such detection reagents may be formulated to detect expression products of these genes at either at the protein or nucleic acid (e.g., mRNA) level. As such, reagents may include: antibodies or specific binding portions thereof (e.g., detectably labeled antibodies), other specific protein binding agents (e.g., ligands or soluble receptors), nucleic acid probes for use in hybridization analysis, e.g., northern blot analysis, microarray analysis, and the like; primer pairs for use in PCR assays, e.g., quantitative PCR assays as detailed above); etc.

As noted above, the subject kits typically further include instructions for using the components of the kit to practice the subject methods, e.g., to prepare nucleic acid samples for perform the mutation process according to aspects of the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the components noted above, the kits may also include one or more control samples and reagents, e.g., two or more control samples. Such control samples may take any form, e.g., additional cell lines having known marker profiles, negative and positive control samples for use in analyzing gene expression data, etc. Any convenient control sample may be employed in the subject kits.

Biological Deposits

Cell lines described in this application have been deposited with the American Type Culture Collection ("ATCC"; P.O. Box 1549, Manassas, Va. 20108, USA) under the Budapest Treaty. The cell line 4D20.8 (also known as ACTC84) was deposited at the ATCC at passage 11 on Jul. 23, 2009 and has ATCC Accession No. PTA-10231. The cell line SM30 (also known as ACTC256) was deposited at the ATCC on Jul. 23, 2009 at passage 12 and has ATCC Accession No. PTA-10232. The cell line 7SMOO32 (also known as ACTC278) was deposited at the ATCC at passage 12 on Jul. 23, 2009 and has ATCC Accession No. PTA-10233. The cell line E15 (also known as ACTC98) was deposited at the ATCC at passage number 20 on Sep. 15, 2009 and has ATCC Accession No. PTA-10341. The cell line MEL2 (also known as ACTC268) was deposited at the ATCC at passage number 22 on Jul. 1, 2010 and has ATCC Accession No. PTA-11150. The cell line SK11 (also known as ACTC250) was deposited at the ATCC at passage number 13 on Jul. 1, 2010 and has ATCC Accession No. PTA-11152. The cell line 7PEND24 (also known as ACTC283) was deposited at the ATCC at passage number 11 on Jul. 1, 2010 and has ATCC Accession No. PTA-11149.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Microarray Analysis of Clonal Human Embryonic Progenitor Lines in a Low Throughput Screen of Chondrogenic Differentiation Conditions The cell lines 10RPE8, 4D20.8, 4D20.9, 4SKEL20, 7PEND12, 7PEND24, 7PEND30, 7PEND9, 7SKEL4, 7SKEL7, 7SMOO25, 7SMOO32, 7SMOO7, 7SMOO9, B16, C4.4, C4ELS5.1, C4ELS5.6, C4ELSR10, C4ELSR2, CMO2, E109, E111, E120, E15, E164, E33, E44, E68, E69, E85, EN1, EN13, EN16, EN18, EN2, EN22, EN23, EN26, EN27, EN31, EN4, EN42, EN47, EN5, EN51, EN55, EN7, EN8, F15, J16, MEL2, MEL2, MW1, RAD20.16, RAD20.19, RAD20.4, RAD20.5, RAD20.6, RAPEND10, RAPEND15, RAPEND18, RASKEL8, RASMO12, RASMO19, SK11, SK17, SK18, SK25, SK31, SK35, SK43, SK44, SK46, SK47, SK49, SK50, SK52, SM17, SM2, SM22, SM28, SM28, SM30, SM33, SM8, T14, T20, T36, T42, T43, T44, T7, U31, W10, W11, W8, Z1, Z11, Z2, and Z3 were screened as described above as "Micromass Differentiation Protocol 1" and a subset were also differentiated as "Pellet Differentiation," and "Alginate Bead Differentiation." In brief, Control cell types were included in the screen including: human bone marrow mesenchymal stem cells passage 3 (Lonza), adipose stem cells (ASCs), dental pulp stem cells (DPSCs), foreskin dermal fibroblasts (Xgene FB), and normal human articular chonodrocytes (NHACs). The cells to be screened as well as the control cell types described above were were synchronized in growth arrest or micromass and pellet chondrogenic conditions in incubators with 5% ambient oxygen as described herein as well as in U.S. patent application Ser. No. 11/604,047 filed on Nov. 21, 2006 and titled "Methods to Accelerate the Isolation of Novel Cell Strains from Pluripotent Stem Cells and Cells Obtained Thereby"; and U.S. patent application Ser. No. 12/504,630 filed on Jul. 16, 2009 and titled "Methods to Accelerate the Isolation of Novel Cell Strains from Pluripotent Stem Cells and Cells Obtained Thereby", each incorporated herein by reference. By way of example, for the conditions to induce synchronization in quiescence, the cell line 7PEND24 (ACTC283) was cultured in Promocell endothelial MV2 media with supplements at concentrations normally recommended by the manufacturer and sold as a complete kit (Cat#C-22022) until the cells reached confluence. Upon reaching confluence, the media was removed and replaced with the same Promocell media but with 10% of the original supplement mix. After three days the media was aspirated and replaced with the same media (i.e. 10% normal supplements) for an additional two days (i.e. five days of quiescence conditions in total). In the case of the cell line 4D20.8 (ACTC84), cells were cultured in DMEM media supplemented with 20% FCS until the cells reached confluence. Upon reaching confluence, the media was removed and replaced with the same DMEM media but with 10% of the original concentration (i.e. 2% FCS). After three days the media was aspirated and replaced with the same media (i.e. DMEM with 2% FCS) for an additional two days (i.e. five days of quiescence conditions in total) or differentiated in chondrogenic conditions as pellets or micromasses for 1, 2, or 14 days. RNA was harvested as described herein and assayed by qPCR and hybridized to Illumina microarrays for gene expression analysis as described herein. Bone marrow mesenchymal stem cells responded to both pellet and micromass chondrogenic conditions with a marked up-regulation of chondrocyte gene expression. Examples of chondrocyte differentiation markers include MGP and PENK which while not specific to cartilage, are nevertheless upregulated during chondrogenesis, and COL2A1, MATN4, EPYC, COL9A2, and LECT1 that are relatively specific to developing cartilage. A comparison of gene expression in the undifferentiated vs 14 days in micromass conditions in the cell line 4D20.8 showed an upregulation of MGP expression of >479x, MATN4 of >10x, PENK of >369x, COL2A1 of >60x, EPYC of >42x, COL9A2 of >25x, LECT1 of >24x, and similarly, with MSCs, the differentiation showed an upregulation of MGP expression of 5x (though the undifferentiated MSCs expressed relatively high basal levels of expression unlike 4D20.8), MATN4 of 20x, PENK of 6x (again, relatively high levels in undifferentiated MSCs compared to no expression in undifferentiated 4D20.8), COL2A1 of 613x, EPYC of 48x, COL9A2 of 117x, LECT1 of 34x. In contract, dermal fibroblasts showed an upregulation of MGP expression of 37x, PENK of 369x, but no expression of COL2A1, EPYC, LECT1, or COL9A2 either before or after experimental treatment. Therefore, unlike dermal fibroblasts, 4D20.8 expressed a wide array of cartilage-specific genes, similar, although not identical to MSCs. Of 24,526 genes assessed, 265 genes showed increased expression during MSC differentiation, 191 increased during D20.8 differentiation, and only 47 genes were in common. Therefore, the cell line 4D20.8 represents a cell line distinct from MSCs, with site-specific LHX8 homeobox gene expression of the palate and mandible and no HOX or PITX1 expression, unlike the MSCs that showed no LHX8 expression, but instead caudal HOX gene expression such as HOXA10, HOXB7, HOXC8, and HOXD13, and PITX1 expression characteristic of the lower extremities. The line 7PEND24 also showed chondrogenic induction at lower levels.

Figure 2A:
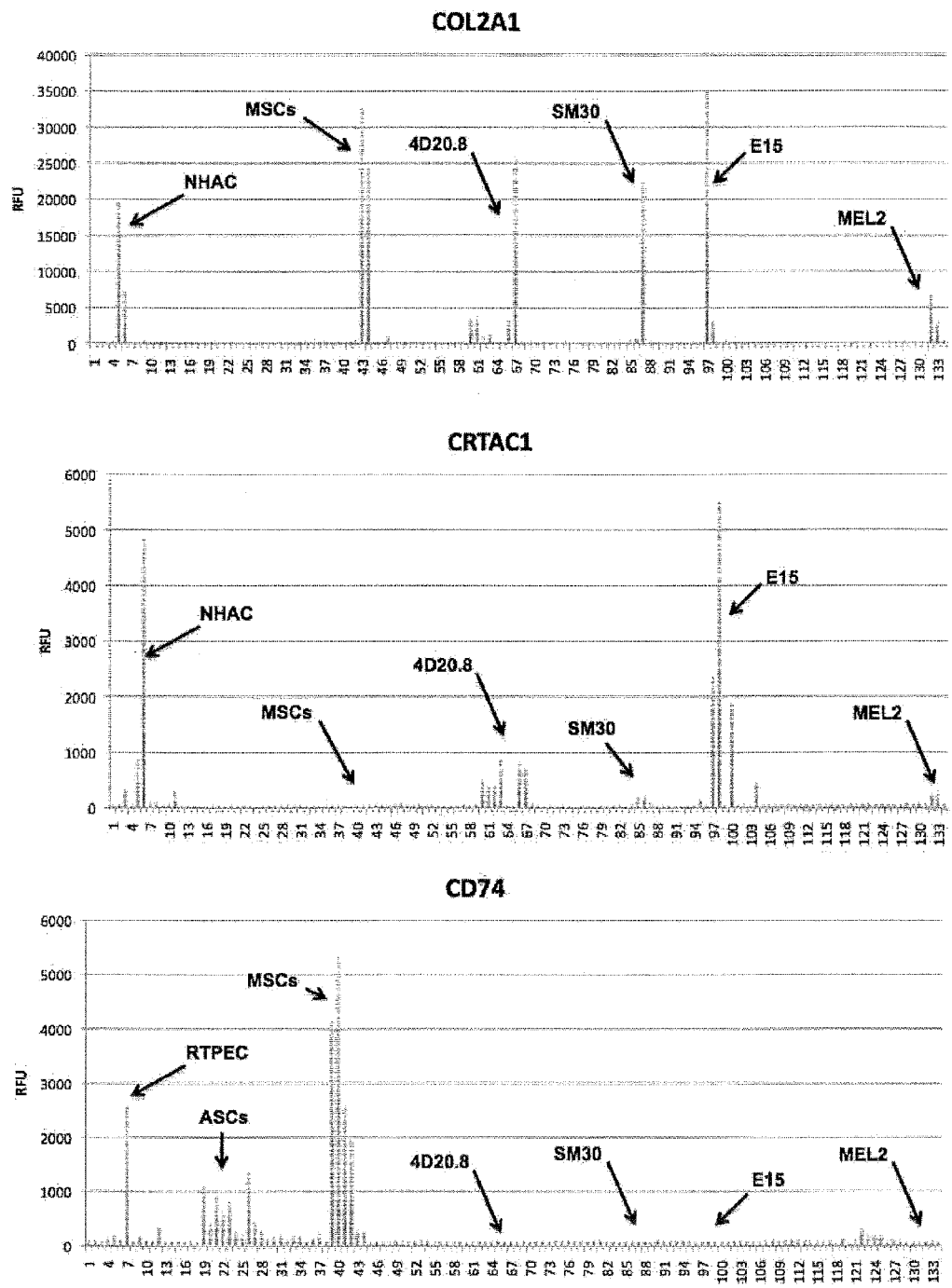
FIG. 2: Relative expression of the cartilage-related genes COL2A1, CRTAC1, CD74, (2A) LECT1, IHH, and LHX8 (2B) are shown in MSC controls along with the lines of the present invention in undifferentiated and differentiated conditions.
Figure 2B:
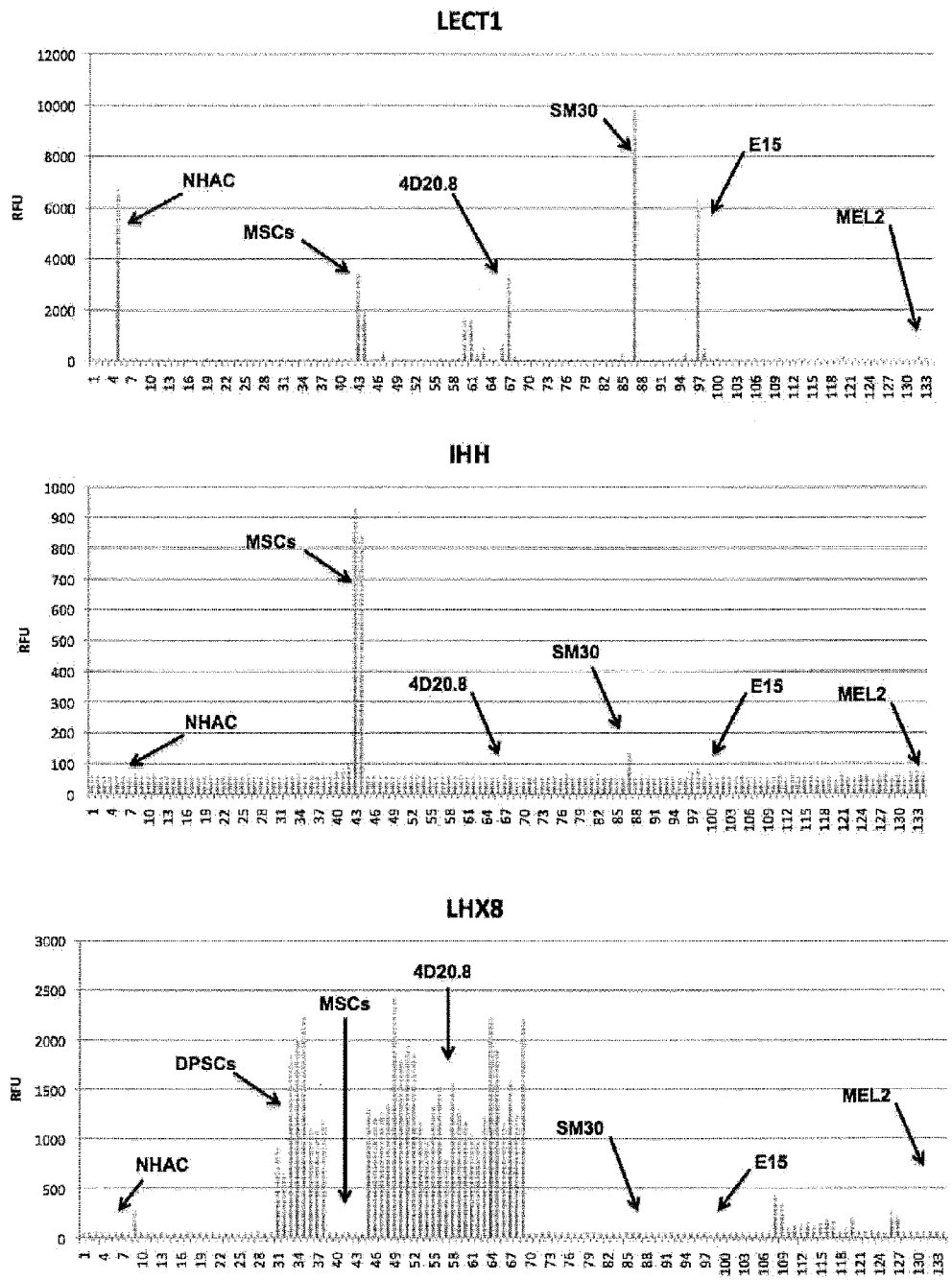
Figure 3:
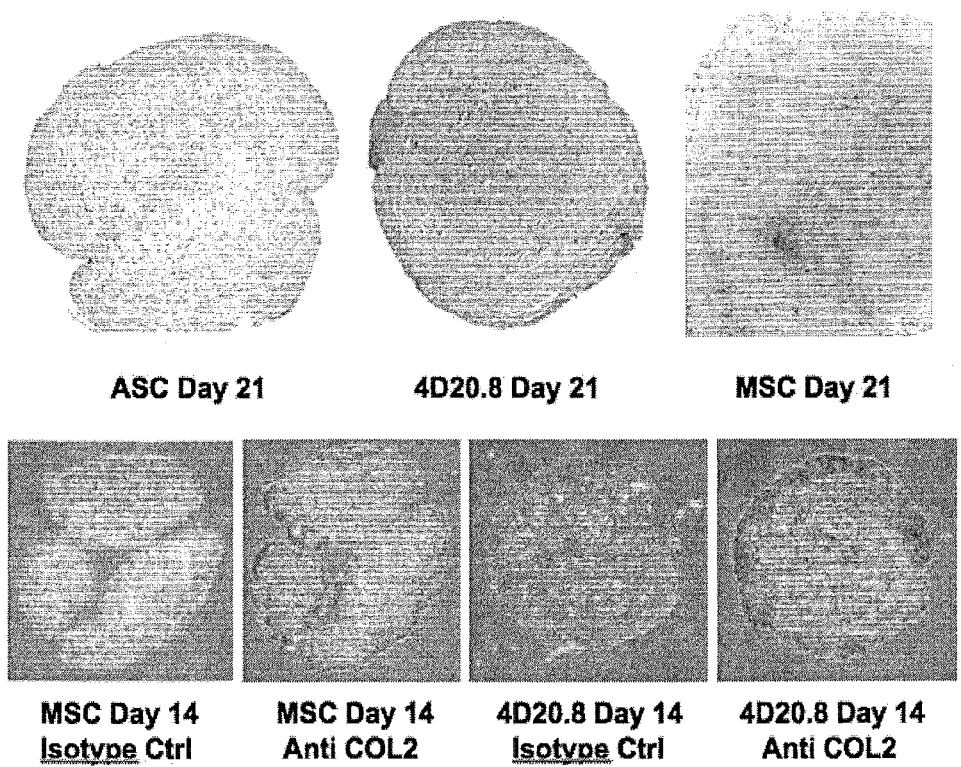
FIG. 3: shows an example of the Safranin O staining of adipose tissue stem cells compared to the lines 4D20.8 at passage 14 compared to MSCs at passage 6 all at day 21 of differentiation as a pellet and immunostaining with isotype controls in day 14 pellets of the line 4D20.8 and MSCs.

Levels of induction of COL2A1 in assayed by microarrays in lines before and after 14 days of chondrogenic conditions along with MSC and normal human articular chondrocyte (NHAC) controls is shown in FIG. 2 in the graph titled "COL2A1." As can also be seen in FIG. 2, the gene for LECT1, a common component of cartilage is also induced in the lines, however, differentially expressed in the lines. CRTAC1, a gene originally characterized as a marker of permanent cartilage (as opposed to hypertrophic chondrocytes) is indeed expressed in NHACs, but not MSCs, but it is expressed in the cell lines of the present invention to varying degrees. The marker IHH that is expressed in hypertrophic chondrocytes, is not expressed in NHACs, is expressed in MSCs, but is not expressed in the cells of the present invention, consistent with their being distinct from MSCs and potentially progenitors to stable cartilage. CD74, a gene originally characterized as a marker of MSCs but not fibroblasts, is expressed in adipose stem cells (ASCs), MSCs, but not NHACs or the cell lines of the present invention. Lastly, LHX8, a marker of mandibular mesenchyme, is not expressed in NHACS, ACSs, but is expressed in dental pulp stem cells (DPSCs) consistent with their origin in mandibular neural crest and is expressed in the line 4D20.8.

After 14 days of micromass and in a subset of these cell lines pellet chondrogenic conditions as described, the lines 7PEND24, 4D20.8, 7SMOO32, MEL2, SK11, SM30, and E15 expressed markedly elevated COL2A1 expression upon induction of differentiation, with 4D20.8, 7SMOO32, MEL2, E15, and SM30 expressing higher relative levels of transcript than normal human articular chondrocytes. Strikingly, the line SM30 expressing >1,000 as much COL2A1 transcript. Bone marrow mesenchymal stem cells at passage 3 expressed little if any transcript though this was observed to vary greatly with the lot and passage number of the cells used as is well-known in the art. No COL2A1 expression was observed in ASCs, DPSCs, or Xgene FBs. The lines express varied markers combinations of markers such as TBX5 and HAND2, markers of mesoderm and of neural crest and therefore are useful in modeling diverse types of chondrogenesis and in clinical cell-based therapy. In addition, they display varied site-specific homeobox genes that generate the site-specific unique mechanical properties of the cartilages in the body. By way of nonlimiting example, the cell line 4D20.8 strongly expresses the marker gene LHX8, a marker of perioral mesenchyme, such as that producing the secondary palate, reconstructing the mandible, or other derivatives of neural crest mandibular mesenchyme including but not limited to: the repair of cleft palate, periodontal disease, reconstructing tooth buds by contributing cells capable of forming the neural crest components of teeth, dermis of the mandibular region, peripheral nerves or melanocytes of the mandibular region, or repairing gingival atrophy.

Example 2

As has been previously demonstrated with hMSCs, the injury and repair of articular cartilage and meniscus after medial or lateral meniscectomy or ACL resection in sheep using the administration of exogenous cells can be determined (Ghosh, et al., Clin. Orthop., Vol. 252, pgs. 101-113, 1990; Little, et al., J. Rheumatol., Vol. 11, pgs. 2199-2209, 1997; both of which are incorporated herein by reference in their entirety). Tolerance in sheep to hES-derived cells is achieved through the prenatal transplantation of hES-derived cells. Escalating doses of hES-iPS-derived embryonic progenitors, such as 7PEND24, 7SMOO32, SM30, E15, 4D20.8, as well as hMSC and HA controls, are injected into the injured joint of the tolerized sheep with one or more pharmaceutical carriers including Hextend, hyaluronan, chondroitin sulfate, chitin, chitosan, or other scaffold/matrix (e.g., decellularized meniscus). The rate of repair of the injury is measured over time in response to escalating dosage. Transplanted cells are evaluated histologically for evidence of rejection, teratoma formation, and efficacy compared to human adult MSCs and vehicle control.

Example 3

Assaying the Stability of Embryonic Chondrocyte Progenitors Over Extended Passage Whereas we were unable to passage adult bone marrow MSCs for >30 doublings, we cultured the cell line of the present invention designated 4D20.8 for over 33 passages. We compared the ability of the cells to induce cartilage as measured by COL2A1 expression and assayed by qPCR as described herein at passage 12 and passage 33. The cells at extended passage produced comparable levels of COL2A1 unlike that of MSCs in parallel experiments. The ability to scale up cells from working cell banks at passage 12 for another 21 passages or more, where each passage is 1.5 doublings, corresponds to approximately 52 doublings or 2e50 greater cells than the working cell bank. The cells are therefore unique in their potential to be commercially scaled for allogeneic transplant in many patients.

Example 4

Screening for Antibodies Recognizing CD Antigens on Selected Chondrogenic Lines of the Present Invention The chondrogenic cell lines of the present invention were assayed in a medium throughput manner against a library of antibodies for CD antigens and the percent positive cells are shown below (Table 2) demonstrating the general utility of the predicted antigens described in U.S. patent application Ser. No. 11/604,047 filed on Nov. 21, 2006 and titled "Methods to Accelerate the Isolation of Novel Cell Strains from Pluripotent Stem Cells and Cells Obtained Thereby"; and U.S. patent application Ser. No. 12/504,630 filed on Jul. 16, 2009 and titled "Methods to Accelerate the Isolation of Novel Cell Strains from Pluripotent Stem Cells and Cells Obtained Thereby", each incorporated herein by reference. However, exceptions can also be identified. In particular, antibodies to the antigen CD56 (NCAM1) binds 80% of the cells in line 4D20.8 while it binds a minority of the other lines tested. This is consistent with the relatively high levels of NCAM1 (Illumina probe ID 4040725) in the microarray data. Antibodies to CD56 are therefore useful in the affinity purification of cells with the gene expression markers of the line 4D20.8 described herein.

TABLE 2

| Marker | 4D20.8 p21 | 7SMOO32 p15 | 7PEND24 p18 | SM30 p15 | SK11 p16 | E15 p27 |
|---|---|---|---|---|---|---|
| αβTCR | 0.00 | 0.00 | 2.29 | 1.04 | 0.32 | 0.15 |
| β2-microglobulin | 85.68 | 86.80 | 91.52 | 95.28 | 90.30 | 92.06 |
| CD25 | 68.81 | 0.71 | 26.60 | 1.09 | 0.22 | 17.30 |
| CD26 | 26.60 | (1.03) | 4.26 | 3.91 | 2.92 | 66.10 |
| CD40 | 8.47 | (1.05) | 9.73 | 4.42 | 41.84 | 79.70 |
| CD49d | 86.26 | 18.48 | 85.29 | 94.74 | 87.16 | 92.03 |
| CD54 | 72.67 | 18.12 | 78.54 | 83.44 | 89.88 | 92.65 |
| CD56 | 79.76 | 0.58 | 25.49 | 3.64 | 14.85 | 0.88 |
| CD62L | 8.69 | 11.38 | 84.53 | 12.32 | 10.85 | 3.20 |
| CD66 (a, b, c, d) | 13.93 | (6.10) | 44.83 | 6.31 | 22.13 | 13.95 |
| CD66b | 41.26 | 23.39 | 77.70 | 24.49 | 63.33 | 4.17 |
| CD70 | 73.85 | 12.50 | 37.38 | 17.59 | 10.45 | 14.82 |
| CD75 | 1.97 | 19.36 | 92.08 | 6.34 | 6.17 | 83.25 |
| CD77 | 43.87 | 23.18 | 73.22 | 3.00 | 3.50 | 0.00 |
| CD81 | 89.96 | 96.94 | 88.86 | 95.82 | 92.59 | 93.19 |
| CD87 | 84.20 | 24.08 | 88.25 | 93.21 | 92.55 | 61.99 |
| CD90 | 89.78 | 15.69 | 0.03 | 87.52 | 17.18 | 92.69 |
| CD94 | 83.91 | 7.90 | 49.67 | 1.08 | 2.01 | 1.11 |
| CD95 | 32.25 | 16.45 | 31.96 | 2.65 | 18.79 | 91.87 |
| CD97 | 6.81 | 0.00 | 0.00 | 1.01 | 11.55 | 61.00 |
| CD99R | 12.69 | 19.97 | 4.99 | 2.64 | 25.51 | 57.54 |
| CD100 | 6.42 | 0.40 | 12.08 | 3.31 | 0.00 | 0.47 |
| CD104 | 53.36 | 0.73 | 0.86 | 84.89 | 1.12 | 68.38 |
| CD108 | 60.08 | 2.83 | 88.36 | 80.03 | 88.41 | 49.56 |
| CD119 | 55.21 | 0.92 | 64.49 | 46.03 | 64.72 | 72.66 |
| CD121a | (2.05) | 1.78 | 4.21 | 26.94 | 64.47 | 27.23 |
| CD121b | 0.00 | 0.30 | 5.17 | 1.08 | 4.28 | 0.00 |
| CD130 | 50.74 | 7.24 | 65.11 | 55.31 | 63.29 | 61.93 |
| CD133 | 2.56 | 54.84 | 9.88 | 2.17 | 3.66 | 0.00 |
| CD141 | 87.72 | 3.89 | 82.09 | 95.37 | 70.32 | 89.28 |
| CD158a | 78.45 | 0.00 | 6.66 | 0.00 | 0.00 | 0.00 |
| CD172b | 70.42 | 5.74 | 89.09 | 77.41 | 87.06 | 60.38 |
| CD195 | 46.67 | 28.43 | 78.15 | 8.27 | 27.56 | 26.37 |
| CD197 | 30.21 | 4.54 | 50.27 | 3.30 | 4.06 | 5.90 |
| CD200 | 29.13 | 0.00 | 2.11 | 6.61 | 66.61 | 0.00 |
| CD201 | 86.37 | 73.21 | 85.31 | 62.43 | 79.90 | 80.94 |
| CD209 | 19.10 | 66.53 | 51.85 | 27.17 | 47.70 | 22.49 |
| CD220 | 49.88 | (0.53) | 23.21 | 10.99 | 26.64 | 60.61 |
| CD273 | 40.48 | 3.67 | 65.30 | 43.16 | 62.46 | 71.83 |
| CD274 | 28.55 | 18.05 | 72.08 | 78.66 | 91.11 | 91.10 |
| Desmin | 3.18 | 53.60 | 2.88 | 5.10 | 12.17 | 1.28 |
| Disialoganglioside GD2 | 85.00 | 0.39 | 0.11 | 56.45 | 0.00 | 12.53 |
| hu MSC (W7C6) | 68.07 | 23.94 | 27.06 | 66.18 | 15.80 | 88.08 |
| hu MSC and NPC (W4A5) | 19.92 | 63.10 | 58.92 | 61.08 | 44.78 | 6.30 |
| hu TNAP (W8B2) | 6.76 | 24.86 | 6.46 | 2.93 | 13.65 | 3.67 |
| MIC A/B | 84.61 | 50.65 | 85.94 | 89.29 | 88.55 | 0.10 |
| TROP-2 | 1.33 | 0.00 | 17.14 | 3.75 | 0.00 | 89.79 |

Example 5

The Discovery of a NNAT Positive Chondrogenic Progenitor Line

The cell line E15 (also known as ACTC98) at passage 17 was expanded by serial passaging in DMEM medium supplemented with 20% serum which is the same medium in which it was originally clonally expanded (see Supplementary Table I, West et al., 2008, Regenerative Medicine vol. 3(3) pp. 287-308, incorporated herein by reference). At passage 14 and 17 the cells were synchronized into quiescence by removing the medium once the cells had reached confluence and replacing the media with fresh DMEM supplemented with a ten-fold reduction of serum (2%). After three days the media was aspirated and replaced with fresh DMEM supplemented with 2% FCS for an additional two days. Cells at the same passage were plated in both micromass and pellet conditions to induce chondrogenesis as described herein. After 14 days of micromass culture, the cell line E15, and normal human articular chondrocytes (NHAC) controls cultured under the same conditions, were assayed by qPCR for the expression specific markers (see Example 6, below). E15 was observed to express >10,000 more COL2A1 mRNA than NHAC controls. Day 14 micromasses were fixed and stained with Safranin O as described below. The samples stained strongly for cartilage proteoglycan. To further characterize the cells, RNA was hybridized to Illumina microarrays as described herein.

Example 6

Low Throughput Screen for Chondrogenic Progenitors Scoring by qPCR

The cell lines of the present invention designated 10RPE8, 4D20.8, 4D20.9, 4SKEL20, 7PEND12, 7PEND24, 7PEND30, 7PEND9, 7SKEL4, 7SKEL7, 7SMOO25, 7SMOO32, 7SMOO7, 7SMOO9, B16, C4.4, C4ELS5.1, C4ELS5.6, C4ELSR10, C4ELSR2, CMO2, E109, E111, E120, E15, E164, E33, E44, E68, E69, E85, EN1, EN13, EN16, EN18, EN2, EN22, EN23, EN26, EN27, EN31, EN4, EN42, EN47, EN5, EN51, EN55, EN7, EN8, F15, J16, MEL2, MEL2, MW1, RAD20.16, RAD20.19, RAD20.4, RAD20.5, RAD20.6, RAPEND10, RAPEND15, RAPEND18, RASKEL8, RASMO12, RASMO19, SK11, SK17, SK18, SK25, SK31, SK35, SK43, SK44, SK46, SK47, SK49, SK50, SK52, SM17, SM2, SM22, SM28, SM28, SM30, SM33, SM8, T14, T20, T36, T42, T43, T44, T7, U31, W10, W11, W8, Z1, Z11, Z2, and Z3 were expanded in vitro >21 doublings of clonal expansion since they were isolated from hES-derived cells, synchronized in quiescence by growing to confluence and replacing the media with media supplemented with a 10-fold reduction in serum or other mitogens as described herein. RNA was extracted from these cells as a control. In a low throughput screen for cells capable of chondogenesis in vitro, cells were cultured in micromass conditions to induce chondrogenesis as described herein for 14 days. RNA from each of these two conditions was converted to cDNA and then examined for expression of genes commonly associated with chondrogenesis (i.e. COL2A1, COMP, CILP, SCX, CRTL1, SOX9, BARX2). Gene-specific primer pair probes were obtained from Invitrogen. Samples for testing were prepared in standard Optical 96-well reaction plates (Applied Biosystems Carlsbad, Calif., PN 4306737) consisting of 30 ng of RNA equivalent of cDNA, 0.4 uM per primer, Ultra-Pure distilled water (Invitrogen), diluted 1:1 with 12.5 ul of Power SYBR Green PCR Master Mix (Applied Biosystems Carlsbad, Calif., Cat#4367659) incorporating AmpliTaq Gold DNA polymerase in a total reaction volume of 25 ul. Real-Time qPCR was run using Applied Biosystems 7500 Real-Time PCR System employing SDSv1.2 software. Amplification conditions were set at 50° C. for 2 min. (stage 1), 95° C. for 10 min. (stage 2), 40 cycles of 95° C. for 15 sec then 60° C. for 1 min (stage 3), with a dissociation stage at 95° C. for 15 sec, 60° C. for 1 min, and 95° C. for 15 sec (stage 4). Ct values for amplification products of genes of interest were normalized to the average Ct value of 3 housekeeping genes (GAPD, RPS10, and GUSB), and gene expression analyzed relative to that of early passage knee-Normal Human Articular Chondrocytes (Lonza) and cultured human bone marrow mesenchymal stem cells.

The Primer sets used to detect chondrogenic genes were those described above: Col2A1 expression expressed as fold-expression compared to cultured early passage normal human articular chondrocytes for the lines screened is shown in FIG. 1. Early passage normal human articular chondrocytes (NHAC) set as 1.0 in value. The expression level of COL2A1 quantified as -fold induction compared to NHACs, was not markedly elevated in the majority of the cell lines but strikingly elevated in a small subset of the lines, namely, 7SMOO32 technical replicate 2 (154x NHAC expression), 7SMOO32 biological replicate 2 (137x NHAC expression), 4D20.8 biological replicate 2 (130x NHAC expression), SM30 (1287x NHAC expression), SM30 biological replicate 2 (13,494x NHAC expression), SM30 technical replicate 2 (1168x NHAC expression), E15 (10,809x NHAC expression), E15 technical replicate 2 (9810x NHAC expression), MEL2 (22x NHAC expression), and SK11 (4x NHAC expression).

Surprisingly, there was little if any correlation of COL2A1 induction with commonly-used markers for chondrogenic induction of mesenchyme such as SOX9. Similarly, markers such as AQP1 speculated to be a marker of chondrogenic mesenchymal cells was present at an RFU value of foreskin dermal fibroblasts that did not induce COL2A1 in micromass chondrogenic conditions and was absent in the cell lines of the present invention prior to and after differentiation. For instance, prior to differentiation, AQP1 expression was absent (RFU 135 which is background) in the line SM30, absent (RFU of 126) in SK11, and absent (RFU 139) in the line E15, at 18-21 doublings of clonal expansion (see West et al., 2008, Regenerative Medicine vol. 3(3) pp. 287-308, supplementary Table II). Neither was the level of expression of SOX9 in the undifferentiated cell lines of the present invention of predictive value in forecasting whether a cell line of the present invention was capable of chondrogenesis. Indeed, no genes could be found in the undifferentiated lines prior to differentiation that correlated sufficiently with the potential of these lines to become chondrocytes to predict such an outcome. The diversity of gene expression markers within the group of SK11, 7SMOO32, 4D20.8, MEL2, SM30, and E15 including site-specific homeobox gene expression, suggest that each line represents a unique and distinguishable type of chondrogenic progenitor. Also surprising was that many of the genes commonly used as markers of in vitro chrondrogenesis such as COMP and CILP were induced in the culture conditions in a nonspecific manner in virtually any cell type including cultured dermal fibroblasts, regardless of whether said dermal fibroblast, for instance, was capable of undergoing true chondrogenesis under the same conditions as evidenced by the expression of COL2A1 and showing histological evidence of cartilage formation. In addition, the cell lines SK11, 7SMOO32, 4D20.8, MEL2, SM30, and E15 were clearly distinguishable from cultured bone marrow MSCs in regard to gene expression markers both before and after differentiation. While the bone marrow MSC is commonly described as ALCAM (CD166) positive, the cell lines of the present invention in the undifferentiated state such as SK11, 7SMOO32, 4D20.8, MEL2, SM30, and E15 showed CD166 expression was absent (RFU 125 which is background) in the line SM30, absent (RFU of 164) in SK11 (see West et al., 2008, Regenerative Medicine vol. 3(3) pp. 287-308, supplementary Table II). Additional differences of the cell lines of the present invention when compared to MSCs, by way of nonlimiting example, is the expression of CD74 that has been demonstrated to be a more precise marker of MSCs than many of the commonly-used markers that are actually not specific (Ishii et al, 2005 BBRC 332:297-303). As shown in Table 3, undifferentiated MSCs indeed expressed very high levels of CD74 transcript, adipocyte stem cells expressed CD74 as well at lower levels, dental pulp stem cells expressed CD74 at the limits of detection, but the transcript was not detected at all in undifferentiated cells of the present invention capable of inducing COL2A1 including SK11, 7SMOO32, 4D20.8, MEL2, SM30, and E15, nor in cultured dermal fibroblasts or in the nonchondrogenic embryonic progenitor line 7SMOO7. An additional nonlimiting example demonstrating the diversity of the lines and the striking differences with the adult stem cell types studied herein, is the expression of the developmental gene NNAT (NM_181689.1) expressed at high levels in the cell line E15, but not in adult stem cells such as MSCs, adipocyte stem cells, dental pulp stem cells, or dermal fibroblasts. Yet another nonlimiting example of the salient differences of the cell lines of the present invention capable of inducing COL2A1 expression from stem cell types in the art, can be seen by measuring the expression of the gene KCNK2 (NM_001017425.2) known to be a marker of MSCs. As shown in Table 3, KCNK2 is expressed at high levels in MSCs, adipocyte stem cells, and dental pulp stem cells, but was not detectable in several of the lines of the present invention capable of inducing the expression of COL2A1 such as SM30, E15, 4D20.8, MEL2, and SK11. A striking difference of the cell lines of the present invention and bone marrow-derived MSCs is also seen in genes that indicate important therapeutic differences in the cell types. MSCs suffer from undergoing transformation into hypertrophic chondrocytes when they differentiate in vitro. Hypertrophic chondrocytes express genes useful in inducing angiogenesis and provide a temporary matrix that is later invaded by osteoblasts to make bone. Therefore, MSCs do not perform well when injected into the joint, or otherwise transplanted into articular cartilage, in an effort to regenerate that tissue for the treatment of joint cartilage trauma, arthritis, or related uses. The cell lines of the present invention when induced by the chondrogenic conditions herein, induced very little if any expression of IHH, a marker of hypertrophic chondrocytes, while MSCs expressed very high levels of IHH transcript. Similarly, the line 4D20.8 did not express detectable levels of COL10A1, another marker of hypertrophic chondrocytes, while MSCs expressed very high levels of the transcript. Therefore, the cell lines of the present invention such as 7SMOO32, 4D20.8, SM30, and E15 show markers that they are superior to MSCs in their ability to differentiate into permanent cartilage for the repair of joint cartilage pathology. Further nonlimiting examples of the differences in the lines SK11, 7SMOO32, 4D20.8, MEL2, SM30, and E15 compared with cultured human bone marrow MSCs, adipocyte stem cells, and adult dental pulp stem cells, is shown in Table 3 or can be seen by comparing the gene expression markers of the cells with those described herein such as in Table 3. Therefore, these results suggest that the cell lines identified in this screen are novel, that the markers commonly used to identify MSCs are not predictive of chondrogenic capacity in human embryonic progenitor cell lines, and that there currently exists no markers that would have predicted that said cell lines would have been the small subset of lines that would respond to chondrogenic stimuli in expressing true markers of chondrogenesis. Evidence is provided in Example 7 of histological evidence of cartilage formation.

Example 7

Histological and Immunochemical Confirmation of Cartilage Formation

Cell lines of the present invention, such as those discovered in the low throughput screen in Example 6 above as showing moderate to robust induction of COL2A1 such as 7PEND24, 7SMOO32, MEL2, SM30, E15, SK11, and 4D20.8 as well as controls such as MSCs, adipocyte stem cells, and other cell lines such as foreskin dermal fibroblasts, Z11, dental pulp stem cells, 7SMOO7, E44 and others were exposed to micromass and pellet chondrogenic conditions as described herein for varying times including 1, 8, 14, and 21 days, and a subset of said pellets when transferred into the kidney capsule of SCID mice to promote extended differentiation. Said micromasses and pellets were fixed in formalin and analyzed histologically with H&E stains, Safranin O staining of proteoglycans as described above, and for immunoreactive COL2A1 using specific antibody and nonspecific antibody as a control. Strong reactivity to Safranin O and/or COL2A1 immunoreactivity was observed in day 14 and 21 pellets of the line 4D20.8 and strong Safranin O staining in day 14 micromasses of the line E15. Surprisingly, the cell line RAD20.6 showed immunoreactivity to COL2A1 and Safranin O staining in a day 14 pellet. FIG. 2 shows an example of the Safranin O staining of adipose tissue stem cells compared to the lines 4D20.8 at passage 14 compared to MSCs at passage 6 all at day 21 of differentiation as a pellet and immunostaining with isotype controls in day 14 pellets of the line 4D20.8 and MSCs.

Example 8

Cell lines of the present invention capable of chondrogenesis were tested for capacity to repair articular cartilage as follows: donated human articular tissue is explanted. $5 \times 10^5$ cells of the lines SM30, E15, and 4D20.8 were spun down in

TABLE 3

A comparison of gene expression markers in human adipocyte stem cells (ACSs), human bone marrow mesenchymal stem cells (MSCs), human adult dental pulp stem cells (DPSCs), cultured human foreskin fibroblasts (Fibro), a clonal hEP line not capable of COL2A1 induction 7SMOO7, and the human embryonic progenitors SM30, E15, 4D20.8, 7SMOO32, MEL2 and SK11 each capable of induced COL2A1 Expression.

| Gene  | ASCs   | MSCs   | DPSCs   | SM30    | E15   | 4D20.8 | 7SMOO32 | MEL2   | SK11  | 7PEND24 | Fibro   | 7SMOO7  |
|-------|--------|--------|---------|---------|-------|--------|---------|--------|-------|---------|---------|---------|
| SOX9  | +717   | +1128  | +639    | +/-214  | +452  | +250   | +1397   | +269   | +386  | +559    | +322    | +731    |
| LHX8  | -81    | -76    | +987    | -84     | ND    | +1194  | -81     | -73    | -79   | -156    | -80     | -93     |
| AQP1  | -108   | -102   | -105    | -105    | -139  | -97    | -106    | -104   | -109  | -97     | -96     | -99     |
| CD166 | +1410  | +2901  | +4031   | -125    | +341  | +2921  | +3265   | +2633  | +1852 | +2261   | +1733   | +2315   |
| ENG   | +3497  | +5521  | +1296   | +2369   | +453  | +2798  | +2302   | +1856  | +820  | +726    | +1729   | +1026   |
| CD90  | +4739  | +6659  | +16270  | +/-282  | +742  | +3589  | +902    | +788   | +617  | -100    | +13439  | +2801   |
| ITGA2 | +563   | +970   | +/-216  | -131    | -176  | -140   | +426    | -52    | -184  | +505    | +/-280  | +/-276  |
| CD74  | +990   | +5093  | +/-220  | -131    | -135  | -88    | -97     | -36    | -108  | -125    | -117    | -150    |
| KCNK2 | +1707  | +2025  | +470    | -107    | -139  | -193   | +382    | -39    | -106  | -108    | +833    | +280    |
| NNAT  | -133   | -93    | -166    | -105    | +1090 | -94    | -117    | -100   | -99   | -134    | -101    | -93     |

Numbers are RFU values. Negative expression indicated by shaded boxes. (ND means No Data)

15 ml conical tube at 400×g for 5 min in 10% FBS/DMEM/F12, and incubated overnight to generate cell aggregates. Six mm diameter cylindrical plugs were cored out from the articular explants with Arthrex Single Use OATS System (Naples, Fla.). A surgical curette was used to make partial thickness defects approximately 2 mm in size in the articular surface. The defects were filled with cell aggregates of SM30, E15, and 4D20.8 or controls consisting of primary human articular chondrocytes, mass cultures of hES-derived chondrocytes, or adult adipose-derived stem cells (hASCs). The cartilage explants were incubated in 10% FBS/DMEM/F12, in the presence or absence of TGF☐3. After 4 weeks, explants were fixed, paraffin-embedded, sectioned, and stained with Safranin O for scoring. Gene expression levels and matrix stains in selected clonal cell lines were higher using the clonal progenitor cell lines SM30, E15, and 4D20.8 than in heterogeneous hESCs and ASCs, and approached levels seen in hACs. In cartilage explants, the repair tissue resembled articular cartilage and was well integrated with surrounding host tissue.

Example 9

Cell lines of the present invention capable of chondrogenesis were tested for capacity to undergo chondrogenesis in an artificial matrix. Cells from the cell lines 4D20.8 and 7PEND24 were expanded, pelleted by centrifugation at low speed, washed with NaCl (155 mM) centrifuged again, and the pellet was resuspended at 20×10$^6$ in 1.2% alginate (Lonza). The cell suspension was drawn into a 1 ml syringe and through a 22 g needle was dispensed dropwise into a CaCl$_2$ bath (102 mM). Gelation is immediate. Beads were washed 3-5× with NaCl (155 mM), then washed once with Chondrogenic medium (without TGF) following immersion in chondrogenic medium. The beads were placed in multiple wells of 6 well plates and fed three days a week for 14 days. Beads were then washed with NaCl multiple times before depolymerization by exposure to sodium citrate (55 mM) for 20 minutes. After spinning, the cell pellet was lysed with RLT (Qiagen) and total RNA extracted using RNeasy micro kits (Qiagen) following a shredding step using QiaShredder to improve yield. COL2A1 expression was determined by qPCR as above. In the case of the cell line 4D20.8, there was a 51-fold increase in COL2A1 expression compared to normal micromass conditions. In the cell line 7SMOO32, there was a 2.88-fold increase in COL2A1 expression using RGD-alginate as compared to normal micromass conditions. In the case of the cell line SK11, there was a 179-fold increase in COL2A1 expression using alginate as compared to normal micromass conditions. In addition to Lonza alginate, RGD-linked alginate (NovaMatrix) beads were also prepared. In the case of 7PEND24, while it only weakly induced COL2A1 in micromass conditions, in alginate beads it showed a 45-fold increase compared to micromass conditions. 7PEND24 encapsulated in RGD-alginate complex did not display enhanced COL2A1 expression over micromass conditions, but did display a 17-fold higher expression of COL2A1 as compared to normal human articular chondrocytes (NHACs). Similarly, 7SMOO32 that was only weakly chondrogenic in micromass conditions, robustly expressed COL2A1 in RGD-alginate beads.

Using the Illumina platform, RGD alginate showed an impressive 449-fold upregulation of COL2A1 in line 4D20.8.

Example 10

To determine the stability of the lines over serial in vitro passaging, the cell lines 4D20.8, E15, SM30, and hbmMSCs were serially passaged with periodic isolation of RNA in the undifferentiated state and in 14 micromasses and alginate beads as described above (Example 9). The cell line 4D20.8 at passage 33 compared to P12 in alginate beads displayed approximately the same levels of COL2A1 while hbmMSCs could not be compared at comparable passages due to senescence.

Example 11

In-vivo s.c. Implantation of Chondrogenic hEPs Encapsulated in Alginate hES cell progenitor lines 4D20.8, E15, SM30, 7PEND24, MEL2 and controls human bone marrow MSCs, and x-Gene skin fibroblasts were scaled, detached, pelleted, and re-suspended in alginate preparations (Lonza 1.2% or NovaMatrix 1.5% with RGD peptide linked alginate) at 20×10$^6$ cells/ml. For gelation and cell encapsulation, a 1 ml sterile syringe was used and the alginate suspension after loading into the syringe was discharged through a 22G needle dropwise into CaCl$_2$ (102 mM) solution or placed in femur shaped silicone molds wetted previously with CaCl$_2$ and then covered with 102 mM CaCl$_2$ for complete rapid gelation.

The femoral shaped constructs were removed from molds and washed with NaCl (155 mM), as were the alginate beads (about 1-2 mm in diameter), followed by immersion in chondrogenic differentiation medium containing dexamethasone 0.1 uM, and human recombinant TGFβ33 (10 ng/ml). Constructs and beads were fed Mon, Wed, and Fri. Twelve days later constructs were implanted s.c. into the shoulder of NOD-SCID mice and at day fourteen beads were implanted similarly.

Six weeks following implantation the tissue was excised, fixed with 4% paraformaldehyde for 24 hours then immersed in 70% alcohol.

Figure 4:
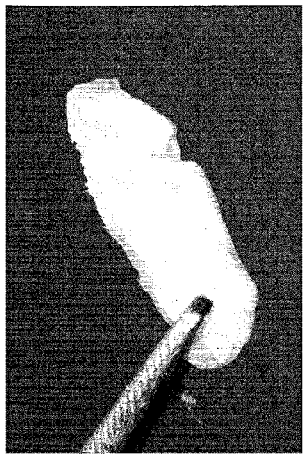
FIG. 4: shows result of in vivo implantation of 4D20.8 RGD-alginate (FIG. 4A), E15 RGD-alginate and SM30 RGD-alginate (FIG. 4B).
Figure 4:
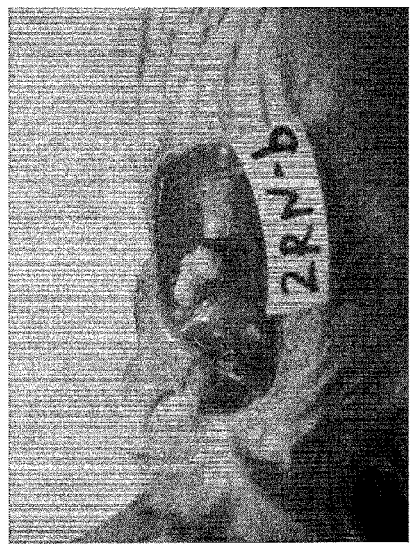
Figure 4:

Macroscopic observation revealed certain hEPC constructs and beads were easily distinguishable from normal fascia underlying skin acquiring a whitish appearance. Exemplary explants for 4D20.8 alginate explant (FIG. 4A).

For histological evaluation samples were paraffin embedded, sectioned into 4 um slices at about 100 um intervals, and placed onto slides which were then stained with hematoxylin and eosin.

Figure 5:
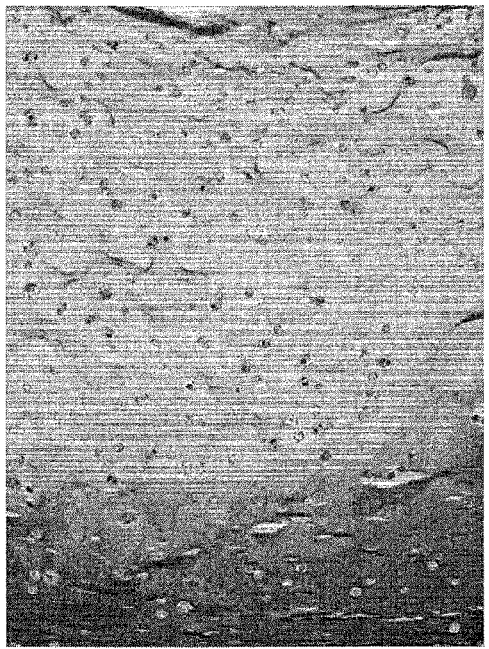
FIG. 5: shows exemplary histological images showing chondrocyte-like appearance similar to that in hyaline cartilage for cell lines 4D20.8 and E15.
Figure 5:
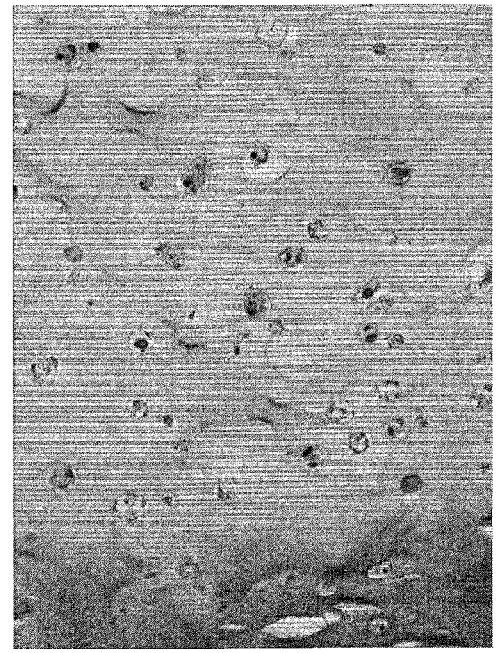
Figure 5:
Figure 5:
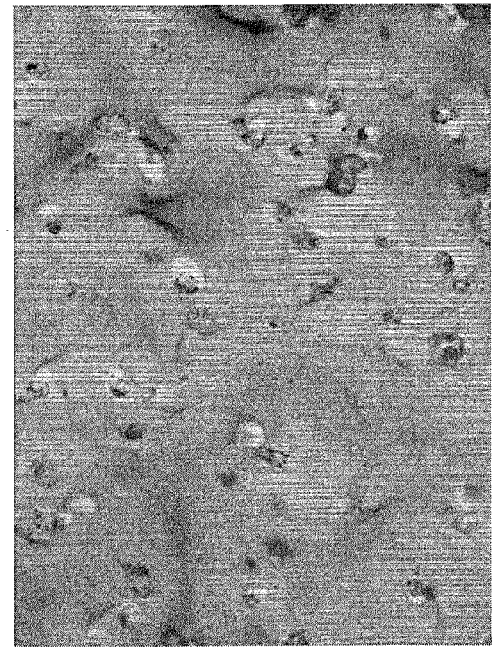

FIG. 5 shows exemplary histological images showing chondrocyte-like appearance similar to that in hyaline cartilage for cell lines 4D20.8 and E15.

TABLE 4

| Parental hES Cell Lines (WA09 or MA03) | ACTC No. | Cell Line | Cell Line Synonyms | Microarray Group | NMF Group Number | NMF Order |
|---|---|---|---|---|---|---|
| MA03 | 50 | B-26 | B26 | Illumina 1 | 4 | 71 |
| MA03 | 51 | B-2 | B2 | Illumina 1 | 9 | 69 |
| MA03 | 52 | B-29 | B-29 | Illumina 1 | 13 | 52 |
| MA03 | 53 | B-7 | B7 | Illumina 1 | 9 | 68 |

TABLE 4-continued

| Parental hES Cell Lines (WA09 or MA03) | ACTC No. | Cell Line | Cell Line Synonyms | Microarray Group | NMF Group Number | NMF Order |
|---|---|---|---|---|---|---|
| MA03 | 54 | B-17 | B17 | Illumina 1 | 8 | 54 |
| MA03 | 55 | B-3 | B3 | Illumina 1 | 4 | 74 |
| MA03 | 56 | B-6 | B6 | Illumina 1 | 15 | 55 |
| MA03 | 57 | B-25 | B25 | Illumina 1 | 4 | 73 |
| MA03 | 58 | B-11 | B11 | Illumina 1 | 4 | 72 |
| MA03 | 59 | B-16 | B16 | Illumina 1 | 7 | 65 |
| MA03 | 60 | B-28 | B28 | Illumina 1 | 12 | 84 |
| MA03 | 61 | B-30 | B30 | Illumina 1 | 14 | 25 |
| MA03 | 62 | 2-2 | 2-2 (Rep1), 2-2 (Rep2), 2.2 | Illumina 1 | 1 | 89 (Rep1), 90 (Rep2) |
| MA03 | 63 | 2-1 | 2.1 | Illumina 1 | 1 | 88 |
| MA03 | 64 | 6-1 | 6.1 | Illumina 1 | 9 | 70 |
| MA03 | 65 | B-12 | B12 | Illumina 1 | 12 | 82 |
| MA03 | 66 | B-4 | B4 | Illumina 1 | 5 | 83 |
| MA03 | 67 | B-14 | B14 | Illumina 1 | NA | NA |
| MA03 | 68 | 5-4 | 5.4 | Illumina 1 | 122 | 32 |
| MA03 | 69 | 4-2 | 4.2 | Illumina 1 | 11 | 37 |
| MA03 | 70 | 2-3 | 2.3 | Illumina 1 | 23 | 94 |
| MA03 | 71 | B-15 | B15 | Illumina 1 | 6 | 22 |
| MA03 | 72 | CM50-4 | CM50.4 | Illumina 1 | NA | NA |
| MA03 | 73 | CM0-3 | CM0.3 | Illumina 1 | 22 | 85 |
| MA03 | 74 | CM0-5 | CM0.5 | Illumina 1 | 22 | 86 |
| MA03 | 75 | CM50-5 | CM50.5 | Illumina 1 | 22 | 87 |
| MA03 | 76 | CM50-2 | CM50.2 | Illumina 1 | NA | NA |
| MA03 | 77 | CM0-2 | CM0.2 | Illumina 1 | 21 | 49 |
| MA03 | 78 | CM30-2 | CM30.2 | Illumina 1 | 10 | 42 |
| MA03 | 79 | CM20-4 | CM20.4 | Illumina 1 | 23 | 93 |
| MA03 | 80 | E26 | E26 | Illumina 1 | NA | NA |
| MA03 | 81 | E71 | E71 | Illumina 1 | NA | NA |
| WA09 | 82 | 4-D20-9 | 4-D20-9 | Illumina 1 | NA | NA |
| WA09 | 83 | 4-SKEL-19 | 4-SKEL-19 | Affymetrix | NA | NA |
| WA09 | 84 | 4-D20-8 | 4-D20-8 | Affymetrix | NA | NA |
| MA03 | 85 | E34 | E34 | Affymetrix | NA | NA |
| MA03 | 86 | E51 | E51 | Illumina 1 | 36 | 24 |
| WA09 | 87 | C4.4 | C4.4 | Affymetrix | NA | NA |
| MA03 | 88 | E3 | E3 | Illumina 1 | 30 | 75 |
| MA03 | 89 | E73 | E73 | Illumina 1 | 30 | 80 |
| MA03 | 90 | E93 | E93 | Illumina 1 | NA | NA |
| MA03 | 91 | E57 | E57 | Illumina 1 | 30 | 79 |
| WA09 | 92 | C4 ELSR #14 | C4 ELSR #14 | Illumina 1 | NA | NA |
| MA03 | 93 | E76 | E76 | Affymetrix | NA | NA |
| MA03 | 94 | E17 | E17 | Illumina 1 | NA | NA |
| MA03 | 95 | E40 | E40 | Illumina 1 | 32 | 28 |
| MA03 | 96 | E8 | E8 | Affymetrix | NA | NA |
| MA03 | 97 | E67 | E67 | Illumina 1 | 30 | 76 |
| MA03 | 98 | E15 | E15 | Illumina 1 | 26 | 26 |
| MA03 | 99 | E45 | E45 | Illumina 1 | 34 | 47 |
| MA03 | 100 | E72 | E72 | Illumina 1 | 7 | 66 |
| MA03 | 101 | E69 | E69 | Illumina 1 | 28 | 16 |
| MA03 | 102 | E75 | E75 | Illumina 1 | 7 | 67 |
| MA03 | 103 | M10 | M10 | Affymetrix | NA | NA |
| MA03 | 104 | M13 | M13 | Affymetrix | NA | NA |
| MA03 | 105 | E19 | E19 | Illumina 1 | 29 | 27 |
| WA09 | 106 | T44 | T44 | Illumina 1 | 114 | 18 |
| MA03 | 107 | E61 | E61 | Illumina 1 | NA | NA |
| WA09 | 108 | C4 ELSR #18 | C4 ELSR #18 | Illumina 1 | 41 | 97 |
| WA09 | 109 | RA-SKEL-8 | RA-SKEL-8 | Illumina 1 | 78 | 147 |
| WA09 | 110 | 4-SKEL-8 | 4-SKEL-8 | Affymetrix | NA | NA |
| WA09 | 111 | RA-PEND-15 | RA-PEND-15 | Illumina 1 | NA | NA |
| MA03 | 112 | E108 | E108 | Affymetrix | NA | NA |
| MA03 | 113 | E35 | E35 | Illumina 1 | NA | NA |
| MA03 | 114 | E33 | E33 | Illumina 1 | 31 | 46 |
| MA03 | 115 | E80 | E80 | Affymetrix | NA | NA |
| MA03 | 116 | E84 | E84 | Illumina 1 | 30 | 78 |
| MA03 | 117 | E109 | E109 | Affymetrix | NA | NA |
| WA09 | 118 | C4 ELS5 #6 | C4 ELS5 #6 | Illumina 1 | 38 | 9 |
| MA03 | 119 | J8 | J8 | Illumina 1 | 65 | 96 |
| WA09 | 120 | T43 | T43 | Illumina 1 | 114 | 17 |
| MA03 | 121 | E10 | E10 | Illumina 1 | NA | NA |
| WA09 | 122 | RA-PEND-6 | RA-PEND-6 | Illumina 1 | NA | NA |
| WA09 | 123 | RA-PEND-10 | RA-PEND-10 | Affymetrix | NA | NA |
| WA09 | 124 | RA-SKEL-3 | RA-SKEL-3 | Illumina 1 | NA | NA |
| WA09 | 125 | RA-SKEL-21 | RA-SKEL-21 | Affymetrix | NA | NA |
| WA09 | 126 | 4-SKEL-4 | 4-SKEL-4 | Affymetrix | NA | NA |
| WA09 | 127 | 4-SKEL-20 | 4-SKEL-20 | Affymetrix | NA | NA |

TABLE 4-continued

| Parental hES Cell Lines (WA09 or MA03) | ACTC No. | Cell Line | Cell Line Synonyms | Microarray Group | NMF Group Number | NMF Order |
|---|---|---|---|---|---|---|
| WA09 | 128 | RA-PEND-4 | RA-PEND-4 | Illumina 1 | NA | NA |
| WA09 | 129 | RA-PEND-18 | RA-PEND-18 | Affymetrix | NA | NA |
| WA09 | 130 | C4 ELS5 #1 | C4 ELS5 #1 | Illumina 1 | 16 | 98 |
| WA09 | 131 | C4 ELSR #12 | C4 ELSR #12 | Illumina 1 | 18 | 99 |
| MA03 | 132 | E163 | E163 | Illumina 1 | NA | NA |
| WA09 | 133 | C4 Mesen. #3 | C4 Mesen. #3 | Illumina 1 | 20 | 45 |
| MA03 | 134 | G6 | G6 | Illumina 1 | NA | NA |
| WA09 | 135 | C4 ELS5 #5 | C4 ELS5 #5 | Illumina 1 | 17 | 100 |
| MA03 | 136 | J16 | J16 | Illumina 1 | 64 | 95 |
| WA09 | 137 | SK46 | SK46 | Illumina 1 | 92 | 186 |
| WA09 | 138 | SK47 | SK47 | Illumina 1 | 93 | 184 |
| WA09 | 139 | EN2 | EN2 | Illumina 1 | 47 | 167 |
| WA09 | 140 | EN26 | EN26 | Illumina 1 | 49 | 160 |
| WA09 | 141 | EN31 | EN31 | Illumina 1 | 52 | 172 |
| WA09 | 142 | SM2 | SM2 | Illumina 1 | 98 | 115 |
| WA09 | 143 | SM4 | SM4 | Illumina 1 | 105 | 109 |
| WA09 | 144 | EN4 | EN4 | Illumina 1 | 54 | 163 |
| WA09 | 145 | EN5 | EN5 | Illumina 1 | 57 | 162 |
| WA09 | 146 | SK52 | SK52 | Illumina 1 | 81 | 203 |
| WA09 | 147 | SK43 | SK43 | Illumina 1 | 81 | 202 |
| WA09 | 148 | SK30 | SK30 | Illumina 1 | 88 | 176 |
| WA09 | 149 | SM42 | SM42 | Illumina 1 | 107 | 116 |
| WA09 | 150 | SM28 | SM28 | Illumina 1 | 101 | 112 |
| WA09 | 151 | SM49 | SM49 | Illumina 1 | 109 | 114 |
| WA09 | 152 | C4 ELSR #10 | C4 ELSR #10 | Affymetrix | NA | NA |
| WA09 | 153 | RA-SKEL-11 | RA-SKEL-11 | Illumina 1 | NA | NA |
| WA09 | 154 | RA-SMO-12 | RA-SMO-12 | Illumina 1 | NA | NA |
| WA09 | 155 | RA-D20-16 | RA-D20-16 | Illumina 1 | 72 | 58 |
| WA09 | 156 | SM22 | SM22 | Illumina 1 | 99 | 110 |
| WA09 | 157 | SK5 | SK5 | Illumina 1 | 94 | 148 |
| WA09 | 158 | SK18 | SK18 | Illumina 1 | 84 | 185 |
| WA09 | 159 | SK50 | SK50 | Illumina 1 | 81 | 199 |
| WA09 | 160 | SK54 | SK54 | Illumina 2 | 89 | 135 |
| MA03 | 161 | J4 | J4 | Illumina 1 | NA | NA |
| WA09 | 162 | SK17 | SK17 | Illumina 1 | 83 | 3 |
| WA09 | 163 | SK26 | SK26 | Illumina 1 | 85 | 198 |
| WA09 | 164 | SK31 | SK31 | Illumina 2 | 89 | 134 |
| WA09 | 165 | SK32 | SK32 | Illumina 1 | 90 | 189 |
| WA09 | 166 | SM25 | SM25 | Illumina 1 | 100 | 107 |
| WA09 | 167 | C4 ELSR #2 (Bio 1) | C4 ELSR #2 (Bio 1) | Illumina 1 | 19 | 102 |
| WA09 | 167 | C4 ELSR #2 (Bio 2) | C4 ELSR #2 (Bio 2) | Illumina 1 | 19 | 103 |
| WA09 | 167 | C4 ELSR #2 (Bio 3) | C4 ELSR #2 (Bio 3) | Illumina 1 | 19 | 101 |
| WA09 | 168 | SK3 | SK3 | Illumina 1 | NA | NA |
| WA09 | 169 | SK53 | SK53 | Illumina 1 | 82 | 193 |
| MA03 | 170 | E44 | E44 | Illumina 1 | 33 | 12 |
| MA03 | 171 | E65 | E65 | Affymetrix | NA | NA |
| MA03 | 172 | J13 | J13 | Illumina 1 | 63 | 5 |
| WA09 | 173 | EN1 | EN1 | Illumina 1 | 45 | 154 |
| WA09 | 174 | EN13 | EN13 | Illumina 1 | 43 | 149 |
| WA09 | 175 | EN42 | EN42 | Illumina 1 | 55 | 164 |
| WA09 | 176 | EN47 | EN47 | Illumina 1 | 56 | 152 |
| WA09 | 177 | SM27 | SM27 | Illumina 1 | NA | NA |
| MA03 | 178 | E50 | E50 | Illumina 1 | 35 | 56 |
| MA03 | 179 | E30 (Bio1) | E30 (Bio1) | Affymetrix | NA | NA |
| MA03 | 179 | E30 (Bio2) | E30 (Bio2) | Illumina 1 | 30 | 77 |
| MA03 | 180 | E122 | E122 | Affymetrix | NA | NA |
| WA09 | 181 | SK61 | SK61 | Illumina 1 | 82 | 190 |
| WA09 | 182 | SM17 | SM17 | Illumina 1 | 96 | 122 |
| WA09 | 183 | SM33 | SM33 | Illumina 1 | 104 | 125 |
| WA09 | 184 | EN7 | EN7 | Illumina 1 | 43 | 150 |
| WA09 | 185 | EN55 | EN55 | Illumina 1 | 61 | 161 |
| WA09 | 186 | T7 | T7 | Illumina 2 | 86 | 14 |
| WA09 | 187 | EN22 | EN22 | Illumina 1 | NA | NA |
| WA09 | 188 | SK58 | SK58 | Affymetrix | NA | NA |
| WA09 | 189 | MW2 | MW2 | Illumina 1 | 67 | 187 |
| WA09 | 190 | SK8 | SK8 | Illumina 1 | 95 | 195 |
| WA09 | 191 | SK20 | SK20 | Illumina 1 | NA | NA |
| WA09 | 192 | SK60 | SK60 | Illumina 1 | 82 | 191 |
| WA09 | 193 | MW6 | MW6 | Illumina 1 | 68 | 188 |
| WA09 | 194 | Z11 (Rep 1) | Z11 (Rep 1) | Illumina 1 | 139 | 104 |
| WA09 | 194 | Z11 (Rep 2) | Z11 (Rep 2) | Illumina 1 | 139 | 105 |
| WA09 | 195 | Z6 | Z6 | Illumina 1 | 138 | 120 |
| WA09 | 196 | W10 | W10 | Illumina 1 | 42 | 166 |

TABLE 4-continued

| Parental hES Cell Lines (WA09 or MA03) | ACTC No. | Cell Line | Cell Line Synonyms | Microarray Group | NMF Group Number | NMF Order |
|---|---|---|---|---|---|---|
| WA09 | 197 | W11 | W11 | Illumina 1 | 117 | 157 |
| WA09 | 198 | T36 | T36 | Illumina 1 | 113 | 20 |
| WA09 | 199 | EN27 | EN27 | Illumina 1 | 50 | 159 |
| WA09 | 200 | Z7 | Z7 | Illumina 1 | 138 | 118 |
| WA09 | 201 | SM44 | SM44 | Illumina 1 | 108 | 113 |
| WA09 | 202 | EN38 | EN38 | Illumina 1 | 53 | 171 |
| WA09 | 203 | SK1 | SK1 | Illumina 1 | 79 | 182 |
| WA09 | 204 | SK44 | SK44 | Illumina 1 | 81 | 201 |
| WA09 | 205 | SK57 | SK57 | Illumina 1 | 87 | 197 |
| MA03 | 206 | J2 | J2 | Affymetrix | NA | NA |
| MA03 | 207 | E68 | E68 | Illumina 1 | 37 | 11 |
| MA03 | 208 | E169 | E169 | Illumina 1 | 28 | 15 |
| MA03 | 209 | E164 | E164 | Illumina 1 | 27 | 53 |
| WA09 | 210 | T42 | T42 | Illumina 1 | 113 | 21 |
| WA09 | 211 | T14 | T14 | Illumina 1 | 111 | 19 |
| WA09 | 212 | RA-D20-6 | RA-D20-6 | Affymetrix | NA | NA |
| WA09 | 213 | Z8 | Z8 | Illumina 1 | 100 | 108 |
| WA09 | 214 | SK40 | SK40 | Illumina 1 | 91 | 183 |
| WA09 | 215 | EN11 | EN11 | Illumina 1 | 42 | 165 |
| WA09 | 216 | EN18 | EN18 | Illumina 1 | 45 | 153 |
| WA09 | 217 | EN23 | EN23 | Illumina 1 | NA | NA |
| WA09 | 218 | SK14 | SK14 | Illumina 1 | 82 | 192 |
| WA09 | 219 | SK10 | SK10 | Illumina 1 | 80 | 181 |
| WA09 | 220 | EN51 | EN51 | Illumina 1 | 59 | 173 |
| WA09 | 221 | EN16 | EN16 | Illumina 1 | 44 | 158 |
| MA03 | 222 | E53 | E53 | Illumina 1 | NA | NA |
| MA03 | 223 | E111 | E111 | Illumina 1 | 24 | 48 |
| WA09 | 224 | SK49 | SK49 | Illumina 1 | NA | NA |
| WA09 | 225 | SM8 | SM8 | Illumina 1 | 110 | 106 |
| WA09 | 226 | RA-D20-5 | RA-D20-5 | Illumina 1 | 74 | 57 |
| WA09 | 227 | RA-D20-24 | RA-D20-24 | Affymetrix | NA | NA |
| WA09 | 228 | W7 | W7 | Affymetrix | NA | NA |
| WA09 | 229 | 4-D20-14 | 4-D20-14 | Illumina 1 | NA | NA |
| WA09 | 230 | RA-D20-19 | RA-D20-19 | Illumina 1 | 73 | 59 |
| WA09 | 231 | T20 | T20 | Affymetrix | NA | NA |
| WA09 | 232 | RA-SMO-19 | RA-SMO-19 | Illumina 1 | NA | NA |
| MA03 | 233 | M11 | M11 | Affymetrix | NA | NA |
| WA09 | 234 | EN9 | EN9 | Illumina 1 | NA | NA |
| WA09 | 235 | Q7 | Q7 | Illumina 1 | 71 | 194 |
| WA09 | 236 | U31 | U31 | Illumina 1 | 116 | 64 |
| WA09 | 237 | EN19 | EN19 | Illumina 1 | 46 | 175 |
| WA09 | 238 | C4 ELS5 #8 | C4 ELS5 #8 | Illumina 1 | 39 | 8 |
| WA09 | 239 | Q8 | Q8 | Illumina 1 | NA | NA |
| WA09 | 240 | SK25 | SK25 | Affymetrix | NA | NA |
| WA09 | 241 | EN20 | EN20 | Affymetrix | NA | NA |
| WA09 | 242 | MW1 | MW1 | Illumina 2 | 66 | 4 |
| WA09 | 243 | C4 ELSR #13 | C4 ELSR #13 | Illumina 1 | 40 | 10 |
| WA09 | 244 | Z3 | Z3 | Affymetrix | NA | NA |
| WA09 | 245 | W8 (Rep 1) | W8 (Rep 1) | Illumina 1 | 120 | 151 |
| WA09 | 245 | W8 (Rep 2) | W8 (Rep 2) | Affymetrix | NA | NA |
| WA09 | 246 | SK28 | SK28 | Illumina 1 | 87 | 196 |
| MA03 | 247 | E120 | E120 | Illumina 1 | 25 | 44 |
| WA09 | 248 | SM51 | SM51 | Illumina 1 | NA | NA |
| WA09 | 249 | EN8 | EN8 | Illumina 1 | NA | NA |
| WA09 | 250 | SK11 | SK11 | Illumina 1 | 81 | 200 |
| WA09 | 251 | EN43 | EN43 | Affymetrix | | |
| WA09 | 252 | 4-D20-3 | 4-D20-3 | Affymetrix | NA | NA |
| WA09 | 253 | EN44 | EN44 | Illumina 1 | NA | NA |
| WA09 | 254 | EN50 | EN50 | Illumina 1 | 58 | 178 |
| WA09 | 255 | Z2 | Z2 | Illumina 1 | 140 | 117 |
| WA09 | 256 | SM30 | SM30 | Illumina 1 | 103 | 124 |
| WA09 | 257 | EN53 | EN53 | Illumina 1 | 60 | 179 |
| WA09 | 258 | SK27 | SK27 | Illumina 1 | 86 | 13 |
| WA09 | 259 | U18 | U18 | Illumina 1 | 115 | 62 |
| WA09 | 260 | SM35 | SM35 | Illumina 1 | NA | NA |
| WA09 | 261 | EN25 | EN25 | Illumina 1 | 48 | 174 |
| WA09 | 262 | C4 ELSR 6 | C4 ELSR 6 | Affymetrix | NA | NA |
| WA09 | 263 | Z1 | Z1 | Illumina 1 | 138 | 119 |
| MA03 | 264 | F15 | F15 | Affymetrix | NA | NA |
| WA09 | 265 | RA-SKEL-9 | RA-SKEL-9 | Illumina 1 | NA | NA |
| MA03 | 266 | E85 | E85 | Affymetrix | NA | NA |
| WA09 | 267 | W4 | W4 | Illumina 1 | 88 | 177 |
| WA09 | 268 | MEL-2 | MEL-2 | Affymetrix | NA | NA |
| WA09 | 269 | LS2 | LS2 | Illumina 1 | NA | NA |
| WA09 | 270 | 7-SKEL-4 | 7-SKEL-4 | Illumina 2 | 129 | 130 |
| WA09 | 271 | 7-SKEL-7 | 7-SKEL-7 | Illumina 2 | 129 | 132 |

TABLE 4-continued

| Parental hES Cell Lines (WA09 or MA03) | ACTC No. | Cell Line | Cell Line Synonyms | Microarray Group | NMF Group Number | NMF Order |
|---|---|---|---|---|---|---|
| WA09 | 272 | 7-PEND-9 | 7-PEND-9 | Illumina 2 | 125 | 128 |
| WA09 | 273 | 7-PEND-16 | 7-PEND-16 | Illumina 2 | 125 | 127 |
| WA09 | 274 | 7-SKEL-6 | 7-SKEL-6 | Illumina 2 | 129 | 131 |
| WA09 | 275 | LS3 | LS3 | Illumina 1 | | |
| WA09 | 276 | 7-SMOO-19 | 7-SMOO-19 | Illumina 2 | 131 | 140 |
| WA09 | 277 | 7-SMOO-29 | 7-SMOO-29 | Illumina 2 | 134 | 141 |
| WA09 | 278 | 7-SMOO-32 | 7-SMOO-32 | Illumina 2 | 135 | 136 |
| WA09 | 279 | 7-SMOO-33 | 7-SMOO-33 | Illumina 1 | NA | NA |
| WA09 | 280 | 7-SMOO-4 | 7-SMOO-4 | Illumina 1 | NA | NA |
| WA09 | 281 | 7-SMOO-9 | 7-SMOO-9 | Illumina 2 | 134 | 142 |
| WA09 | 282 | 7-SMOO-17 | 7-SMOO-17 | Illumina 1 | NA | NA |
| WA09 | 283 | 7-PEND-24 | 7-PEND-24 | Illumina 2 | 124 | 156 |
| WA09 | 284 | 7-SKEL-32 | 7-SKEL-32 | Illumina 1 | NA | NA |
| WA09 | 285 | 7-SMOO-13 | 7-SMOO-13 | Illumina 1 | NA | NA |
| WA09 | 286 | 7-SMOO-25 | 7-SMOO-25 | Illumina 2 | 132 | 168 |
| WA09 | 287 | 7-SMOO-12 | 7-SMOO-12 | Illumina 2 | 130 | 138 |
| WA09 | 288 | 7-PEND-30 | 7-PEND-30 | Illumina 2 | 126 | 126 |
| WA09 | 289 | 7-SKEL-25 | 7-SKEL-25 | Illumina 1 | | |
| WA09 | 290 | 7-SMOO-6 | 7-SMOO-6 | Illumina 2 | 136 | 139 |
| WA09 | 291 | 7-SMOO-26 | 7-SMOO-26 | Illumina 2 | 133 | 137 |
| WA09 | 292 | 7-SMOO-22 | 7-SMOO-22 | Illumina 1 | NA | NA |
| WA09 | 293 | 7-SMOO-8 | 7-SMOO-8 | Illumina 1 | NA | NA |
| WA09 | 294 | 7-SKEL-14 | 7-SKEL-14 | Illumina 1 | NA | NA |
| WA09 | 295 | 7-SKEL-11 | 7-SKEL-11 | Illumina 1 | NA | NA |
| WA09 | 296 | 7-SKEL-2 | 7-SKEL-2 | Illumina 2 | 127 | 129 |
| WA09 | 297 | 7-SKEL-22 | 7-SKEL-22 | Illumina 2 | 128 | 133 |
| WA09 | 298 | 7-SMOO-7 | 7-SMOO-7 | Illumina 2 | 137 | 1 |
| WA09 | 299 | 7-PEND-12 | 7-PEND-12 | Illumina 2 | 124 | 155 |
| WA09 | 300 | 7-SMOO-27 | 7-SMOO-27 | NA | NA | NA |
| WA09 | 301 | 7-PEND-13 | 7-PEND-13 | NA | NA | NA |
| WA09 | 302 | 7-PEND-11 | 7-PEND-11 | NA | NA | NA |
| WA09 | 303 | 7-PEND-15 | 7-PEND-15 | NA | NA | NA |
| WA09 | 304 | 7-PEND-32 | 7-PEND-32 | NA | NA | NA |
| WA09 | 305 | 7-PEND-26 | 7-PEND-26 | NA | NA | NA |
| WA09 | 306 | 7-SKEL-24 | 7-SKEL-24 | NA | NA | NA |
| WA09 | 307 | 7-PEND-10 | 7-PEND-10 | NA | NA | NA |
| WA09 | 308 | 7-PEND-23 | 7-PEND-23 | NA | NA | NA |
| | 309 | 10-RPE-9 | 10-RPE-9 | NA | NA | NA |
| | 310 | 10-RPE-8 | 10-RPE-8 | NA | NA | NA |
| WA09 | 311 | RA-PEND-19 | RA-PEND-19 | NA | NA | NA |
| MA03 | NA | X4.1 | X4.1 | Illumina 1 | 3 | 29 |
| MA03 | NA | X4.3 | X4.3 | Illumina 1 | 3 | 31 |
| MA03 | NA | B-10 | B-10 | Illumina 1 | 3 | 30 |
| MA03 | NA | B-1 | B-1 | Illumina 1 | 2 | 39 |
| MA03 | NA | X4 | X4 | Illumina 1 | 121 | 40 |
| MA03 | NA | X5 | X5 | Illumina 1 | 123 | 81 |
| MA03 | NA | B-20 | B-20 | Illumina 1 | 6 | 23 |
| MA03 | NA | B-22 | B-22 | Illumina 1 | 10 | 41 |
| MA03 | NA | X6 | X6 | Illumina 1 | 10 | 43 |
| MA03 | NA | CM10.1 | CM10.1 | Illumina 1 | 11 | 33 |
| MA03 | NA | X2 | X2 | Illumina 1 | 11 | 34 |
| MA03 | NA | B-27 | B-27 | Illumina 1 | 11 | 35 |
| MA03 | NA | B-9 | B-9 | Illumina 1 | 11 | 36 |
| MA03 | NA | X4.4 | X4.4 | Illumina 1 | 11 | 38 |
| MA03 | NA | E31 | E31 | Illumina 1 | 21 | 51 |
| MA03 | NA | CM10-4 | CM10-4 | Illumina 1 | 23 | 91 |
| MA03 | NA | CM30-5 | CM30-5 | Illumina 1 | 23 | 92 |
| MA03 | NA | EN28 | EN28 | Illumina 1 | 51 | 170 |
| WA09 | NA | Q4 | Q4 | Illumina 1 | 69 | 143 |
| WA09 | NA | Q6 | Q6 | Illumina 1 | 70 | 180 |
| WA09 | NA | RA-PEND-17 (Bio 1) | RA-PEND-17 (Bio 1) | Illumina 1 | 75 | 146 |
| WA09 | NA | RA-PEND-17 (Bio 2) | RA-PEND-17 (Bio 2) | Affymetrix | | |
| WA09 | NA | RA-SKEL-18 (Rep 1) | RA-SKEL-18 (Rep1) | Illumina 1 | 76 | 144 |
| WA09 | NA | RA-SKEL-18 (Rep 2) | RA-SKEL-18 (Rep 2) | Affymetrix | NA | NA |
| WA09 | NA | RA-SKEL-6 | RA-SKEL-6 | Illumina 1 | 77 | 145 |
| WA09 | NA | SM19 | SM-19 | Illumina 1 | 97 | 121 |
| WA09 | NA | SM29 | SM-29 | Illumina 1 | 102 | 111 |
| WA09 | NA | SM40 | SM-40 | Illumina 1 | 106 | 123 |
| WA09 | NA | T23 | T-23 | Illumina 1 | 112 | 60 |
| WA09 | NA | T4 | T-4 | Illumina 1 | 112 | 61 |
| WA09 | NA | U30 | U-30 | Affymetrix | 116 | 63 |
| WA09 | NA | W2 | W-2 | Illumina 1 | 118 | 169 |

TABLE 4-continued

| Parental hES Cell Lines (WA09 or MA03) | ACTC No. | Cell Line | Cell Line Synonyms | Microarray Group | NMF Group Number | NMF Order |
|---|---|---|---|---|---|---|
| WA09 | NA | W3 | W-3 | Illumina 1 | 119 | 2 |
| MA03 | NA | E11 | E-11 | Illumina 1 | 21 | 50 |
| WA09 | NA | SK15 | SK15 | Affymetrix | NA | NA |
| MA03 | NA | E55 | E55 | Affymetrix | NA | NA |
| MA03 | NA | E132 | E132 | Affymetrix | NA | NA |
| WA09 | NA | RA-SMO-10 | RASMO10 | Affymetrix | NA | NA |
| WA09 | NA | RA-SMO-14 | RASMO14 | Affymetrix | NA | NA |
| WA09 | NA | W9 | W9 | Affymetrix | NA | NA |
| WA09 | NA | MW4 | MW4 | Affymetrix | NA | NA |
| WA09 | NA | SK16 | SK16 | Affymetrix | NA | NA |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of producing cartilage, the method comprising culturing a clonally-purified embryonic progenitor cell line; wherein said cell line is negative for the expression of one or more of the genes selected from the group consisting of: CD74, CD90, CD166, ITGA2, and KCNK2; wherein said cell line is selected from the group consisting of: SM30, E15, 4D20.8, 7SM0032, MEL2, SK11 and combinations thereof; and wherein said culturing comprises culture under cartilage producing conditions for an amount of time effective to induce cartilage production from said cells.

2. The method of claim 1, wherein the embryonic progenitor cell line is negative for the expression of CD74.

3. The method of claim 2, wherein the embryonic progenitor cell line is further negative for the expression of one or more genes selected from the group consisting of: HOX genes and PITX1.

4. The method of claim 3, wherein the embryonic progenitor cell line generates cartilage in the absence of COL10A1 marker expression.

5. The method of claim 1, wherein the cartilage producing condition is selected from one or more of the group consisting of: chondrocyte culture conditions; impregnating the embryonic progenitor cell line into synthetic matrices or biological resorbable immobilization vehicles; and placing the embryonic progenitor cell line into a molded structure.

6. The method of claim 1, wherein the method further comprises transplanting the cartilage produced by the embryonic progenitor cell line to a subject.

* * * * *